US008785707B2

(12) United States Patent
Cabiac et al.

(10) Patent No.: US 8,785,707 B2
(45) Date of Patent: Jul. 22, 2014

(54) CATALYST BASED ON A CRYSTALLIZED MATERIAL WITH HIERARCHIZED AND ORGANIZED POROSITY AND ITS USE IN OLIGOMERIZATION OF LIGHT OLEFINS

(75) Inventors: Amandine Cabiac, Lyons (FR); Alexandra Chaumonnot, Lyons (FR); Laurent Simon, Villeurbanne (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 798 days.

(21) Appl. No.: 12/994,194

(22) PCT Filed: Apr. 28, 2009

(86) PCT No.: PCT/FR2009/000501
§ 371 (c)(1),
(2), (4) Date: Feb. 1, 2011

(87) PCT Pub. No.: WO2009/153421
PCT Pub. Date: Dec. 23, 2009

(65) Prior Publication Data
US 2011/0172482 A1 Jul. 14, 2011

(30) Foreign Application Priority Data

May 28, 2008 (FR) ...................................... 08 02951

(51) Int. Cl.
*C07C 2/12* (2006.01)
*B01J 29/04* (2006.01)
*C10G 50/00* (2006.01)
*B01J 29/40* (2006.01)
*B01J 35/02* (2006.01)
*B01J 29/70* (2006.01)
*B01J 29/06* (2006.01)
*B01J 37/00* (2006.01)

(52) U.S. Cl.
CPC ................ *C07C 2/12* (2013.01); *B01J 29/041* (2013.01); *B01J 37/0009* (2013.01); *C10G 50/00* (2013.01); *B01J 29/40* (2013.01); *B01J 35/023* (2013.01); *B01J 2229/42* (2013.01); *B01J 29/7007* (2013.01); *C07C 2529/40* (2013.01); *B01J 37/0045* (2013.01); *C07C 2529/70* (2013.01); *B01J 29/06* (2013.01)
USPC ................ 585/531; 502/63; 502/74; 502/77; 502/78; 502/232; 502/254; 502/258; 585/520; 585/530; 585/532; 585/533

(58) Field of Classification Search
USPC ................ 585/502, 520, 531, 532, 533, 530; 502/63, 74, 77, 78, 232, 254, 258
See application file for complete search history.

(56) References Cited

U.S. PATENT DOCUMENTS

| | | | | |
|---|---|---|---|---|
| 5,134,243 A * | 7/1992 | Bhore et al. | ................... | 585/533 |
| 5,849,258 A * | 12/1998 | Lujano et al. | ................. | 423/700 |
| 5,902,564 A | 5/1999 | Lujano et al. | | |
| 6,669,924 B1 * | 12/2003 | Kaliaguine et al. | ........... | 423/702 |
| 6,805,851 B1 * | 10/2004 | Muller et al. | ................. | 423/705 |
| 6,866,925 B1 | 3/2005 | Chane-Ching | | |
| 7,141,232 B2 * | 11/2006 | Miller et al. | ................... | 423/716 |
| 2001/0031241 A1 | 10/2001 | Lacombe et al. | | |
| 2006/0030477 A1 | 2/2006 | Chaumonnot et al. | | |
| 2006/0292054 A1 | 12/2006 | Chaumonnot et al. | | |
| 2007/0244347 A1 * | 10/2007 | Ying et al. | ....................... | 585/17 |
| 2009/0029847 A1 | 1/2009 | Euzen et al. | | |
| 2009/0232720 A1 | 9/2009 | Chaumonnot et al. | | |

FOREIGN PATENT DOCUMENTS

| | | |
|---|---|---|
| EP | 1 108 678 A1 | 6/2001 |
| EP | 1 627 852 A1 | 2/2006 |
| EP | 1 627 853 | 2/2006 |
| WO | WO 01/32558 A1 | 5/2001 |
| WO | WO 01/38223 A1 | 5/2001 |
| WO | WO 2006/128989 A1 | 12/2006 |

OTHER PUBLICATIONS

Xie, et al., "On the Synthesis and Characterization of ZSM-5/MCM-48 Aluminosilicate Composite Materials" in J. Mater. Chem., 2004, 14, 863-870—available on-line Feb. 4, 2004.*
Haber, et al., "Manual of Methods and Procedures for Catalyst Characterization" in Pure & Appl. Chem., 67, 1257-1306, (1995)—month unknown.*
Lide, CRC Handbook of Chemistry and Physics, 2011 Internet Version, D. R. Lide, ed., avaialble on-line at www.knovel.com—month unknown.*
Hawley's Condensed Chemical Dictionary, John Wiley & Sons, 14th ed., 2002—avaialble on-line at www.knovel.com—month unknown.*

(Continued)

*Primary Examiner* — In Suk Bullock
*Assistant Examiner* — Bradley Etherton
(74) *Attorney, Agent, or Firm* — Millen, White, Zelano & Branigan, P.C.

(57) ABSTRACT

A catalyst that comprises at least one binder and at least one crystallized material with hierarchized and organized porosity in the fields of microporosity and mesoporosity is described, whereby said crystallized material consists of at least two elementary spherical particles, each of said particles comprising a mesostructured silicon-oxide-based matrix that has a mesopore diameter of between 1.5 and 30 nm and that has microporous and crystallized walls with a thickness of between 1 and 60 nm, whereby said elementary spherical particles have a maximum diameter of 200 microns. Said catalyst is used in a process for oligomerization of an olefinic feedstock that contains hydrocarbon molecules that have 2 to 12 carbon atoms per molecule.

18 Claims, No Drawings

(56) References Cited

OTHER PUBLICATIONS

Liu, Y. et al., "Steam-stable MSU-S Aluminosilicate Mesostructures Assembled from Zeolite ZSM-5 and Zeolite Beta Seeds," Angew. Chem. Int. Ed., 2001, vol. 40, No. 7, pp. 1255-1258.

Perez-Pariente, J. et al., "Organising disordered matter: strategies for ordering the network of mesoporous materials," C. R. Chimie, 2005, vol. 8, pp. 269-278.

Zheng, J. et al., "Hydrothermally stable MCM-41 analogue with extensive embedded voids," Catalysis Today, 2004, vol. 93-95, pp. 529-534.

International Search Report of PCT/FR2009/000558 (Sep. 24, 2009).

D. Trong on et al., "An Example of Mesostructured Zeolite Material: UL-TS-1," Microporous and Mesoporous Materials, vol. 44-45 (2001) pp. 435-444.

H. IK Lee et al., "Synthesis of Highly Stable Mesoporous Aluminosilicates from Commercially Available Zeolites and Their Application to the Pyrolysis of Woody Biomass," Catalysis Today, vol. 132 (2008) pp. 68-74.

H. Zhang et al., "Preparation and Characterization of Beta/MCM-41 Composite Zeolite with a Stepwise-Distributed Pore Structure," Powder Technology, vol. 183 (2008) pp. 73-78.

\* cited by examiner

CATALYST BASED ON A CRYSTALLIZED MATERIAL WITH HIERARCHIZED AND ORGANIZED POROSITY AND ITS USE IN OLIGOMERIZATION OF LIGHT OLEFINS

TECHNICAL FIELD

This invention relates to a catalyst that is based on a crystallized metallosilicate material that has a hierarchized and organized porosity in the field of microporosity and mesoporosity. Said catalyst is implemented in a process for oligomerization of a light olefinic feedstock.

PRIOR ART

In the quest for new aluminosilicate materials, the so-called "mesostructured" materials, discovered at the beginning of the 1990s, represent a seductive alternative (G. J. of A. A. Soler-Illia, C. Sanchez, B. Lebeau, J. Patarin, Chem. Rev., 2002, 102, 4093). Actually, owing to so-called "soft chemistry" synthesis methods, amorphous mesoporous materials whose size and morpohology of the pores are monitored have been obtained. These mesostructured materials are thus generated at low temperature by the coexistence in aqueous solution or in polar solvents of inorganic precursors with structuring agents, generally molecular or supramolecular, ionic or neutral surfactants. The monitoring of the electrostatic interactions or by hydrogen bonds between the inorganic precursors and the structuring agent jointly linked to hydrolysis/condensation reactions of the inorganic precursor leads to a cooperative assembly of organic and inorganic phases that generate micellar aggregates of surfactants of uniform size that is monitored within an inorganic matrix. This cooperative self-assembly phenomenon, governed by, i.a., the concentration of structuring agent, can be induced by gradual evaporation of a solution of reagents whose structuring agent concentration is less than the critical micellar concentration, which can lead to, for example, the formation of a mesostructured powder after atomization of the solution (aerosol technique). The release of the porosity is then obtained by elimination of the surfactant, the latter being carried out conventionally by processes for chemical extraction or by heat treatment. Based on the nature of inorganic precursors and the structuring agent that is employed as well as the operating conditions that are imposed, several families of mesostructured materials have been developed. For example, the M41S family—initially developed by Mobil (J. S. Beck, J. C. Vartuli, W. J. Roth, M. E. Leonowicz, C. T. Kresge, K. D. Schmitt, C. T.-W. Chu, D. H. Olson, E. W. Sheppard, S. B. McCullen, J. B. Higgins, J. L. Schlenker, J. Am. Chem. Soc., 1992, 114, 27, 10834), consisting of mesoporous materials obtained via the use of ionic surfactants such as quaternary ammonium salts, having a generally hexagonal structure, cubic or lamellar, pores with a uniform size encompassed in a range of 1.5 to 10 nm and amorphous walls with a thickness on the order of 1 to 2 nm—has been extensively studied. Likewise, the use of block-copolymer-type amphiphilic macromolecular structuring agents has led to the development of the family of materials referred to as SBA, whereby these solids are characterized by a generally hexagonal, cubic or lamellar structure, pores with a uniform size encompassed in a range of 4 to 50 nm, and amorphous walls with a thickness encompassed in a range of 3 to 7 nm.

It has been shown, however, that although exhibiting particularly advantageous textural and structural properties (in particular for the treatment of heavy feedstocks), the mesostructured aluminosilicate materials that are thus obtained developed a catalytic activity that was similar in all respects to that of their homologues with non-organized porosity (D. Zaho, J. Feng, Q. Huo, N. Melosh, G. H. Fredrickson, B. F. Chmelke, G. D. Stucky, Science, 1998, 279, 548; Y.-H. Yue, A. Gédéon, J.-L. Bonardet, J. B. d'Espinose, N. Melosh, J. Fraissard, Stud. Surf. Sci. Catal., 2000, 129, 209). Numerous works have therefore been undertaken for the purpose of developing materials that have a microporosity that is zeolitic in nature and a mesostructured porosity so as to benefit simultaneously from the catalytic properties that are specific to zeolites and catalytic properties and primarily textural properties of the organized mesoporous phase.

A large number of synthesis techniques that make it possible to generate materials that have this bi-porosity have thus been listed in the literature (U.S. Pat. No. 6,669,924; Z. Zhang, Y. Han, F. Xiao, S. Qiu, L. Zhu, R. Wang, Y. Yu, Z. Zhang, B. Zou, Y. Wang, H. Sun, D. Zhao, Y. Wei, J. Am, Chem. Soc., 2001, 123, 5014; A. Karlsson, M. Stöcker, R. Schmidt, Micropor. Mesopor. Mater., 1999, 27, 181; P. Prokesova, S. Mintova, J. Cejka, T. Bein, Micropor. Mesopor. Mater., 2003, 64, 165; D. T. On, S. Kaliaguine, Angew. Chem. Int Ed., 2002, 41, 1036). From an experimental standpoint, unlike the previously cited "aerosol" technique, the thus defined aluminosilicate materials with hierarchized porosity are not obtained by a gradual concentration of the inorganic precursors and the structuring agent(s) within the solution where they are present but are conventionally obtained by direct precipitation within an aqueous solution or in polar solvents by varying the value of the critical micellar concentration of the structuring agent. In addition, the synthesis of these materials that are obtained by precipitation requires a curing stage in an autoclave as well as a stage for filtration of the generated suspension. The elementary particles that are usually obtained do not have a uniform shape and are generally characterized by a size that generally varies between 200 and 500 nm and sometimes more.

The processes for oligomerization of the light olefins intended for the production of olefins of higher molecular weight are used extensively in the field of refining and petrochemistry for the purpose of upgrading the light olefins in terms of bases for gasoline-, kerosene- or gas-oil-type fuels, or else in terms of solvent. These oligomerization reactions are conducted in the presence of a catalyst, most often a solid catalyst. The olefins are combined into dimers, trimers, tetramers, etc., the degree of polymerization of the olefins depending on the type of catalyst that is used and the operating conditions of temperature and pressure that are imposed. The advantage of the oligomerization process, relative to other processes in the field of refining and petrochemistry leading to the same product range and well known to one skilled in the art, resides in the fact that the thus obtained compounds are free of sulfur and contain very few aromatic compounds. The solid oligomerization catalysts that are often cited in literature are acidic catalysts whose major examples in the field of oligomerization of light olefins are the "solid substrate-impregnated phosphoric acid" catalysts (for example, U.S. Pat. No. 2,913,506 and U.S. Pat. No. 3,661, 801), the silica-aluminas (for example, the U.S. Pat. Nos. 4,197,185, 4,544,791, and EP 0 463 673), the zeolites (for example, the U.S. Pat. No. 4,642,404 and U.S. Pat. No. 5,284, 989), and, to a lesser extent, the heteropolyanions (for example, the patent IN 170 903).

The impregnated phosphoric acid-type catalysts on a solid substrate (SPA) have a good oligomerization activity as well as a high yield of products that can be upgraded in the gasoline fraction. These catalysts are difficult to manipulate, however, in particular at the time of unloading, because of their tendency to cake in the presence of olefins. The impregnated phosphoric acid-type catalysts on a solid substrate degrade during the reaction and cannot be regenerated.

The heteropolyanion-type catalysts are used for the oligomerization reaction of light olefins. These catalysts are not thermally stable and therefore lead to weak conversions and oligomers with a limited degree of polymerization due to the restricted working temperature.

The silica-alumina-type catalysts have fairly variable porosity characteristics that produce different reactivities. However, their large pore volumes and pore sizes generally make them good candidates for the production of gasoline or jet fuel. For example, for the oligomerization of propylene, the patent EP 0 463 673 claims the use of an amorphous silica-alumina with a specific surface area of between 500 and 1,000 m$^2$/g, a total pore volume of between 0.3 and 0.6 ml/g, a mean pore diameter that is at most equal to approximately 1 nm, and no pore having a diameter of greater than 3 nm.

Finally, the zeolite-based catalysts lead to oligomers having more limited connecting rates than the catalysts cited above because of their selectivity of shape in the micropores. This is favorable for the production of gas oils that have to exhibit a correct cetane index but not very favorable, for example, in the production of gasoline that has to exhibit a good octane number. However, the narrow porosity of the zeolites, favorable to the oligomerization reactions for the production of linear chains that can be incorporated in the gas oil fractions, becomes problematic at the diffusional level according to the size of the zeolite crystals, i.e., the length of pores as shown by O'Connor et al. in Stud. Surf. Sci. Catal., G. Öhlman, H. Pfeifer, R. Fricke, Elsevier, 1991, 65, and it results in a reduction in yields in terms of linear chains that can be incorporated in the gas oil fraction.

SUMMARY OF THE INVENTION

This invention has as its object a catalyst that comprises at least one binder and at least one crystallized material with hierarchized and organized porosity in the fields of microporosity and mesoporosity, whereby said crystallized material consists of at least two elementary spherical particles, each of said particles comprising a meso structured, silicon-oxide-based matrix, having a mesopore diameter of between 1.5 and 30 nm and having microporous and crystallized walls with a thickness of between 1 and 60 nm, said elementary spherical particles having a maximum diameter of 200 microns. The crystallized walls consist of zeolitic entities at the origin of the microporosity of the material. Said zeolitic entities comprise at least one zeolite that contains silicon and at least one element X that is selected from among aluminum, iron, boron, titanium and germanium, and/or at least one related solid. In a very preferred manner, said zeolitic entities comprise at least one zeolite that contains silicon and aluminum. The catalyst according to the invention preferably comes in the form of extrudates that preferably have a diameter of between 0.5 and 5 mm, and more particularly between 0.7 and 2.5 mm.

This invention also has as its object a process for oligomerization of an olefinic feedstock that contains hydrocarbon molecules that have 2 to 12 carbon atoms per molecule.

ADVANTAGE

It has been discovered, surprisingly enough, that a catalyst that comprises at least one binder and at least one crystallized material with hierarchized and organized porosity leads to improved catalytic performances, in particular in terms of yield of the gas oil fraction in a reaction for oligomerization of an olefinic feedstock that contains hydrocarbon molecules that have 2 to 12 carbon atoms per molecule, and in a preferred manner that contains 2 to 8 carbon atoms per molecule. In particular, such a catalyst makes it possible to increase significantly the yield of the gas oil fraction relative to the one that is obtained by employing an existing catalyst in the state of the art. The cetane index that reflects the linearity of the hydrocarbon chains, which are present in the gas oil fraction, and that represents the quality of the gas oil fraction is also advantageously improved relative to the index that a gas oil fraction that is obtained by this reaction generally has. The use of the catalyst according to the invention in a process for oligomerization of an olefinic feedstock that contains hydrocarbon molecules having 2 to 12 carbon atoms per molecule, and in a preferred manner having 2 to 8 carbon atoms per molecule, makes possible the production of an oligomerate (the oligomerate is the product of the reaction) of very good quality that can advantageously be integrated into the gas oil pool of a refinery after distillation at the suitable fraction point.

In contrast, the crystallized material with hierarchized and organic porosity that is present in the catalyst according to the invention and that is formed by a mesostructured inorganic matrix, with a silicon oxide base and with microporous and crystallized walls, simultaneously has structural, textural and acido-basicity properties that are specific to the materials of the family of zeolite and to the so-called mesostructured materials. The silicon-oxide-based matrix that forms each of the elementary spherical particles of the material according to the invention comprises, in addition to silicon, at least one element X that is selected from among aluminum, iron, germanium, titanium and boron, whereby X is advantageously aluminum. The crystallized material with hierarchized and organized porosity that is present in the catalyst according to the invention then has acido-basicity properties that are superior to the acido-basicity properties exhibited by aluminosilicate materials with amorphous walls, lacking crystallized zeolitic entities and prepared according to the synthesis protocols that are well known to one skilled in the art using inorganic precursors of silica and alumina. Furthermore, the presence within the same spherical particle with a micrometric, and even nanometric, size of mesopores organized in a microporous and crystallized inorganic matrix leads to a preferred access of the reagents and products of the reaction at microporous sites during the use of said crystallized material as an element that is present in the catalyst according to the invention in a process for oligomerization of light olefinic feedstocks that contain hydrocarbon molecules that have 2 to 12 carbon atoms per molecule, and in a preferred manner 2 to 8 carbon atoms per molecule.

TECHNIQUES OF CHARACTERIZATION

The crystallized material that comprises silicon with constituent hierarchized and organized porosity of the catalyst according to the invention is characterized by several analysis techniques and in particular by low-angle x-ray diffraction (low-angle XRD), by large-angle x-ray diffraction (XRD), by nitrogen volumetric analysis (BET), by Transmission Electron Microscopy (TEM), and by X fluorescence (XF).

The technique of low-angle x-ray diffraction (values of the angle 2θ of between 0.5 and 3°) makes it possible to characterize the periodicity on the nanometric scale that is generated by the organized mesoporosity of the crystallized material that is present in the catalyst according to the invention. In the following disclosure, the x-ray analysis is done on powder with a diffractometer that operates by reflection and that is equipped with a rear monochromator by using the radiation of copper (wavelength of 1.5406 Å). The peaks that are usually observed on the diffractograms that correspond to a given value of the angle 2θ are combined with inter-reticular distances $d_{(hkl)}$ that are characteristic of the structural symmetry of the material, ((hkl) being the Miller indices of the reciprocal network) by Bragg's equation: $2 d_{(hkl)}*\sin(\theta)=\eta*\lambda$. This indexing then makes it possible to determine the mesh parameters (abc) of the direct network, the value of these parameters being based on the hexagonal, cubic or vermicular structure that is obtained and that is characteristic of the periodic organization of the mesopores of the crsytallized material that is present in the catalyst according to the invention.

The large-angle x-ray diffraction technique (values of angle 2θ of between 5 and 70°) makes it possible to characterize a crystallized solid that is defined by the repetition of an individual pattern or an elementary mesh on the molecular scale. As for the low-angle x-ray diffraction, the peaks that are observed on the diffractograms that correspond to a given value of the angle 2θ are combined with inter-reticular distances $d_{(hkl)}$ that are characteristic of the structural symmetry(ies) of the material, ((hkl) being the Miller indices of the reciprocal network) by Bragg's equation: $2 d_{(hkl)}*\sin(\theta)=\eta*\lambda$. This indexing then makes it possible to determine the mesh parameters (abc) of the direct network. The large-angle XRD analysis is therefore adapted to the structural characterization of the constituent zeolitic entities of the crystallized wall of the matrix of each of the elementary spherical particles that constitute the material that is present in the catalyst according to the invention. In particular, it makes it possible to access the diameter of the micropores of the zeolitic entities.

The nitrogen volumetric analysis that corresponds to the physical adsorption of nitrogen molecules in the porosity of the material via a gradual increase of pressure at constant temperature provides information on the particular textural characteristics (pore diameter, type of porosity, specific surface area) of the material that is present in the catalyst according to the invention. In particular, it makes it possible to access the total value of the micropore and mesopore volumes of the material that is present in the catalyst according to the invention. The form of the nitrogen adsorption isotherm and the hysteresis loop can provide information on the presence of the microporosity that is linked to the zeolitic entities that constitute the crystallized walls of the matrix of each of the spherical particles of the material that is present in the catalyst according to the invention and on the nature of the mesoporosity. The quantitative analysis of the microporosity of the material according to the invention is performed starting from the "t" method (Lippens-De Boer method, 1965) or "$\alpha_s$" method (method proposed by Sing), which correspond to the initial adsorption isotherm transforms as described in the work "*Adsorption by Powders and Porous Solids. Principles, Methodology and Applications,*" written by F. Rouquerol, 3. Rouquerol and K. Sing, Academic Press, 1999. These methods make it possible to access in particular the value of the micropore volume that is characteristic of the microporosity of the material that is present in the catalyst according to the invention as well as the specific surface area of the sample. The reference solid that is used is a LiChrospher Si-1000 silica (M. Jaroniec, M. Kruck, J. P. Olivier, *Langmuir,* 1999, 15, 5410). Relative to the mesostructured matrix, the difference between the value of the diameter of the mesopores φ and the correlation distance between mesopores d defined by low-angle XRD as described above makes it possible to access the value e where $e=d-\phi$ and is characteristic of the thickness of the crystallized walls of the mesostructured matrix of the material that is present in the catalyst according to the invention. Likewise, the curve $V_{ads}$ (ml/g)=f($\alpha_s$) that is obtained via the method $\alpha_s$ cited above is characteristic of the presence of microporosity within the material that is present in the catalyst according to the invention and leads to a value of the micropore volume that is encompassed in a range of 0.01 to 0.4 ml/g. The determination of the total micropore and mesopore volume and of the micropore volume as described above leads to a value of the mesopore volume of the material that is present in the catalyst according to the invention in a range of 0.01 to 1 ml/g, preferably in a range of 0.01 to 0.80 ml/g.

The analysis by Transmission Electron Microscopy (TEM) is a technique that is also extensively used for characterizing the organized mesoporosity of the crystallized material that is present in the catalyst according to the invention. The latter allows the formation of an image of the solid that is studied, whereby the observed contrasts are characteristic of the structural organization, the texture, the morphology, or else the chemical composition of the observed particles, whereby the resolution of the technique reaches at most 0.2 nm. In the following disclosure, the TEM photos will be produced from microtomic cross-sections of the sample so as to display a cross-section of an elementary spherical particle from the material that is present in the catalyst according to the invention. The analysis of the image also makes it possible to access the parameters d, φ, and e that are characteristic of the mesostructured matrix defined above. The analysis of the image also makes it possible to display the presence of the constituent zeolitic entities of the walls of the material present in the catalyst according to the invention.

The composition of the crystallized material that is present in the catalyst according to the invention can be determined by X fluorescence (XF).

DESCRIPTION OF THE INVENTION

This invention has as its object a catalyst that comprises at least one binder and at least one crystallized material with hierarchized and organized porosity in the fields of microporosity and mesoporosity, whereby said crystallized material consists of at least two elementary spherical particles, each of said particles comprising a mesostructured silicon-oxide-based matrix having a mesopore diameter of between 1.5 and 30 nm and having microporous and crystallized walls with a thickness of between 1 and 60 nm, whereby said elementary spherical particles have a maximum diameter of 200 microns.

Material with hierarchized and organized porosity is defined within the terms of this invention as a material that is present in the catalyst according to the invention and that has a double porosity on the scale of each of said spherical particles: a mesoporosity, i.e., the presence of organized pores on the mesoporous scale that have a uniform diameter of between 1.5 and 30 nm and preferably between 2 and 20 nm, distributed homogeneously and uniformly in each of said particles (meso structuring) and a zeolitic-type microporosity whose characteristics (structural type of the zeolite, chemical composition of the zeolitic framework) are based on the zeolitic entities that constitute the crystallized walls of the matrix of each of the spherical particles of the material that is present in the catalyst according to the invention. The material that is present in the catalyst according to the invention also has an intraparticulate and interparticulate textural macroporosity. It should be noted that a porosity that is microporous in nature can also result from the interleaving of the surfactant, used during the preparation of the material that is present in the catalyst according to the invention, with the inorganic wall at the level of the organic-inorganic interface that is developed during the mesostructuring of the inorganic component of said material that is present in the catalyst according to the invention. Advantageously, none of the spherical particles that constitute the material that is present in the catalyst according to the invention has macropores.

The silicon-oxide-based matrix, encompassed in each of the spherical particles that constitute the material that is present in the catalyst according to the invention, is mesostructured: it has mesopores that have a uniform diameter, i.e., identical for each mesopore, encompassed between 1.5 and 30 nm, and preferably between 4 and 30 nm, and very preferably between 5 and 20 nm, distributed homogeneously and uniformly in each of the spherical particles. The material that is located between the mesopores of each of said spherical particles is microporous and crystallized and forms walls, or panels, whose thickness is between 1 and 60 nm, preferably between 2.5 and 30 nm, and in a very preferred manner between 4 and 30 nm. The thickness of the walls corresponds to the distance that separates a first mesopore from a second mesopore, whereby the second mesopore is the pore that is the closest to said first mesopore. The organization of the mesoporosity that is described above leads to a structuring of the silicon-oxide-based matrix, which can be hexagonal, vermicular or cubic, and preferably vermicular. The small-angle XRD analysis makes it possible to calculate the distance d for correlation between the organized mesopores of said material: the distance d for correlation between the organized mesopores of said material is between 6 and 50 nm, preferably between 8 and 30 nm, and in a very preferred manner between 9 and 25 nm.

According to the invention, the silicon-oxide-based matrix that forms each of the spherical particles of the material that is present in the catalyst according to the invention has crystallized walls that consist exclusively of zeolitic entities, which are at the origin of the microporosity that is present with each of the spherical particles of the material that is present in the catalyst according to the invention. Any related zeolite or solid that develops properties of acidity and, in particular, but in a non-exhaustive way, those listed in "Atlas of Zeolite Framework Types," 6$^{th}$ Edition, 2007, Ch. Baerlocher, L. B. McCusker & D. H. Olson, Amsterdam: Elsevier can be used for the formation of zeolitic entities that constitute exclusively the crystallized walls of the matrix of each of the particles of the material that is present in the catalyst according to the invention, since the solubilization of the precursor elements of these entities, namely at least one structuring agent, at least one silicic precursor, and at least one precursor of at least one element X, selected from among aluminum, iron, germanium, titanium and boron, whereby X is advantageously aluminum, according to stage a) of the first process for preparation of the crystalline material with hierarchized and organized porosity described below; since obtaining the zeolitic nanocrystals of maximum nanometric size that is equal to 60 nm starting from at least one structuring agent, at least one silicic precursor, and at least one precursor of at least one element X that is selected from among aluminum, iron, germanium, boron and titanium, whereby X is advantageously aluminum, according to stage a') of the second process for preparation of the crystallized material with hierarchized and organized porosity that is described below; and since the redispersion in zeolitic crystal solution according to stage a") of the third process for preparation of the crystallized material with hierarchized and organized porosity as described below, all lead to obtaining a stable solution, i.e., clear or colloidal, and atomizable. The zeolitic entities that constitute exclusively the crystallized walls of the matrix of each of the particles of the material present in the catalyst according to the invention and at the origin of the microporosity of the latter preferably comprise at least one zeolite that is selected from among the metallosilicates ZSM-5, ZSM-11, ITQ-13, MCM-22, SSZ-44, SSZ-35, ZSM-22, ZSM-23, ZBM-30, ZSM-35, ZSM-48, ZSM-57, EU-1, EU-2, EU-11, beta, zeolite A, Y, USY, VUSY, SDUSY, mordenite, NU-87, NU-88, NU-86, NU-85, IM-5, IM-12, IZM-2, and ferrierite and/or at least one related solid that is selected from among the silicoaluminophosphates SAPO-11 and SAPO-34. In a very preferred manner, the zeolitic entities that integrally constitute the crystallized and microporous walls of the matrix of each of the particles of the material present in the catalyst according to the invention comprise at least one zeolite that is selected from among the structural-type metallosilicates MEL, MFI, ITH, BEA, NES, EUO, ERI, FER, CHA, MFS, MWW, MTT, TON, SFF, STF and MOR and in a very preferred manner selected from among the zeolites of the structural type TON, MTT, BEA, MFS, MFI, MOR and FER. Among the MEL-structural-type zeolites, the ZSM-11 zeolite is preferred. Among the MFI-structural-type zeolites, the ZSM-5 zeolite is preferred. Among the ITH-structural-type zeolites, the ITQ-13 zeolite is preferred (U.S. Pat. No. 6,471,941). Among the NES-structural-type zeolites, the NU-87 zeolite is preferred. Among the EUO-structural-type zeolites, the EU-1 zeolite is preferred. Among the ERI-structural-type zeolites, the erionite zeolite is preferred. Among the FER-structural-type zeolites, the ferrierite and ZSM-35 zeolites are preferred. Among the CHA-structural-type zeolites, the chabazite zeolite as well as the SAPO-34 silicoaluminophosphate are preferred. Among the MFS-structural-type zeolites, the ZSM-57 zeolite is preferred. Among the MWW-structural-type zeolites, the MCM-22 zeolite is preferred. Among the MTT-structural-type zeolites, the ZSM-23 zeolite is preferred. Among the TON-structural-type zeolites, the ZSM-22 zeolite is preferred. Among the MOR-structural-type zeolites, the mordenite zeolite is preferred. These zeolites and their methods of preparation are well known to one skilled in the art.

According to the invention, the silicon-oxide-based matrix that forms each of the elementary spherical particles of the material that is present in the catalyst according to the invention comprises silicon and at least one element X that is selected from among aluminum, iron, germanium, boron and titanium, preferably aluminum. In a preferred manner, X is silicon. Thus, the zeolitic entities that constitute exclusively the crystallized walls of the matrix of each of the spherical particles of the material that is present in the catalyst according to the invention and that is at the origin of the microporosity of said material comprise at least one zeolite that contains silicon and at least one element X that is selected from among aluminum, iron, germanium, boron and titanium, preferably aluminum and/or at least one related solid. When said zeolitic entities contain silicon and aluminum (X=Al), the matrix of said material that is present in the catalyst according to the invention is a crystallized aluminosilicate.

Zeolite or a related solid that are well known to one skilled in the art are defined as the mass of crystallized microporous oxide solids whose constituent atomic elements of the inorganic framework have a coordinance IV. By definition, the designation "zeolite" is attributed to said silicic or metallosilicic microporous oxide solids, preferably aluminosilicic solids. Likewise, the designation "related solid" relates to the mass of crystallized microporous oxide solids whose constituent atomic elements of the inorganic framework have a coordinance IV, whereby said uniquely silicic or metallosilicic, preferably aluminosilicic, microporous oxide solids are excluded. Any zeolite or related solid that has at least one trivalent atomic element at the origin of the presence of a negative charge of said framework and that can be compensated by a positive charge of a protonic nature can develop acidity properties. In particular, the metallosillicate-type zeolites, preferably aluminosilicate zeolites, and the related silicoaluminophosphate-type solids develop such properties.

The mesostructuring of the crystallized material with hierarchized and organized porosity that is present in the catalyst according to the invention can be of the vermicular, cubic, or hexagonal type based on the nature of the surfactant that is used for the implementation of the material that is present in the catalyst according to the invention.

According to the invention, said elementary spherical particles that constitute the crystallized material with hierarchized and organized porosity and that is present in the catalyst according to the invention have a maximum diameter that is equal to 200 microns, preferably less than 100 microns, advantageously between 50 nm and 20 µm, very advantageously between 50 nm and 10 µm, and in an even more advantageous manner between 50 nm and 3 µm. More specifically, they are present in the material that is present in the catalyst according to the invention in the form of aggregates.

Said crystallized material with hierarchized and organized porosity that is present in the catalyst according to the invention advantageously has a specific surface area of between 70 and 1,100 m$^2$/g and in a very advantageous manner between 100 and 1,000 m$^2$/g.

Said crystallized material with hierarchized and organized porosity that is present in the catalyst according to the invention advantageously has a mesopore volume that is measured by nitrogen volumetric analysis of between 0.01 and 1 ml/g, preferably between 0:01 and 0.80 ml/g, and a micropore volume that is measured by nitrogen volumetric analysis of between 0.01 and 0.4 ml/g.

The catalyst according to the invention also comprises at least one binder that is usually amorphous or poorly crystallized; in general, it consists of at least one refractory oxide in amorphous or poorly crystallized form. Said binder is generally selected from the group that is formed by alumina, silica, silica-alumina, clays, in particular natural clays such as kaolin or bentonite, magnesia, titanium oxide, boron oxide, zirconia, aluminum phosphates, titanium phosphates, zirconium phosphates, and carbon. Said binder can also be selected from among the aluminates. In a preferred manner, the binder is an alumina in all of its forms that are known to one skilled in the art, and preferably gamma-alumina. The binder can also consist of a mixture of at least two of the oxides that are cited above, for example silica-alumina. In a preferred manner, a binder that contains alumina, in all of the forms that are known to one skilled in the art, for example gamma-alumina, will be used. According to the invention, the content by weight of the crystallized material with hierarchized and organized porosity in the catalyst according to the invention is between 50 and 99%, preferably between 55 and 97%, and in an even more preferred manner between 70 and 95%, and the content by weight of binder in the catalyst according to the invention is between 1 and 50%, preferably between 3 and 45%, and in an even more preferred manner between 5 and 30%.

The catalyst according to the invention advantageously comes in the form of cylindrical or multilobed extrudates such as bilobed, trilobed, or multilobed extrudates of straight or twisted shape or else in the form of crushed powders, tablets, rings, balls, and wheels. In a very preferred manner, the catalyst according to the invention comes in the form of extrudates with a diameter of between 0.5 and 5 mm and more particularly between 0.7 and 2.5 mm. In a preferred manner, the cylindrical shape is used.

The catalyst according to the invention also advantageously comprises at least one metal that is selected from among the metals of groups IA, IIA, JIB, VIIB and VIII. Among the metals of group IA, sodium is preferred. Among the metals of group IIA, magnesium, calcium, strontium, and barium are preferred. Among the metals of group JIB, zinc and cadmium are preferred. Among the metals VIIB, rhenium is preferred. Among the metals of group VIII, iron, cobalt, nickel, platinum, palladium, rhodium and ruthenium are preferred. The content by weight of metal(s) is advantageously between 0.01 and 10% by weight and very advantageously between 0.05 and 5% by weight relative to the weight of the crystallized material that is present in the catalyst according to the invention.

This invention also has as its object the preparation of the catalyst according to the invention.

The crystallized material with hierarchized and organized porosity that is present in the catalyst according to the invention is advantageously obtained according to three alternative preparation processes. A first embodiment of the process for preparation of said crystallized material with hierarchized and organized porosity, called "first process for preparation of said material that is present in the catalyst according to the invention" below, comprises: a) the preparation of a clear solution that contains the precursor elements of zeolitic entities, namely at least one structuring agent, at least one silicic precursor, and at least one precursor of at least one element X that is selected from among aluminum, iron, boron, germanium and titanium, whereby X is advantageously aluminum; b) the mixing in solution of at least one surfactant and at least said clear solution that is obtained according to a) such that the ratio of the volumes of inorganic and organic materials $V_{inorganic}/V_{organic}$ is between 0.26 and 4; c) the atomization by aerosol of said solution that is obtained in stage b) for leading to the formation of spherical droplets; d) the drying of said droplets; e) the autoclaving of the particles that are obtained according to d); f) the drying of said particles that are obtained according to e); and g) the elimination of said structuring agent and said surfactant for obtaining a crystallized material with a hierarchized and organized porosity in the fields of microporosity and mesoporosity.

A second embodiment of the process for preparation of said crystalline material with hierarchized and organized porosity, called "second process for preparation of said material that is present in the catalyst according to the invention" below, comprises the stages: a') the preparation, starting from at least one structuring agent, of at least one silicic precursor, and at least one precursor of at least one element X that is selected from among aluminum, iron, boron, germanium and titanium, whereby X is advantageously aluminum, a solution that contains zeolitic nanocrystals with a maximum nanometric size that is equal to 60 nm so as to obtain a colloidal solution in which said nanocrystals are dispersed; b') the solubilization of at least one surfactant and at least said solution that is obtained according to a') such that the ratio of the volumes of inorganic and organic materials $V_{inorganic}/V_{organic}$ is between 0.26 and 4; c') the atomization by aerosol of said solution that is obtained in stage b') for leading to the formation of spherical droplets; d') the drying of said droplets; and g') the elimination of said structuring agent and said surfactant for obtaining a crystallized material with a hierarchized and organized porosity in the fields of microporosity and mesoporosity.

According to a first variant of said second process for preparation of the material that is present in the catalyst according to the invention, said stage d') is advantageously followed by a stage e') that consists in autoclaving the particles obtained according to d') and then a stage f') consisting in initiating drying of said particles that are obtained according to e'), whereby said stage f') is then followed by said stage g').

According to a second variant of said second process for preparation of the material that is present in the catalyst according to the invention, stage b') is implemented by solubilizing at least one surfactant, at least said colloidal solution that is obtained according to stage a'), and at least one clear solution that contains the precursor elements of zeolitic entities, namely at least one structuring agent, at least one silicic precursor, and at least one precursor of at least one element X that is selected from among aluminum, iron, boron, germanium, and titanium, whereby X is advantageously aluminum. Said mixture is produced under conditions such that the ratio of the volumes $V_{inorganic}/V_{organic}$ of inorganic and organic materials that are engaged in this stage b') is between 0.26 and 4. According to this variant, stage d') of said second process for preparation of the material that is present in the catalyst according to the invention is followed by a stage e') that consists in autoclaving the particles that are obtained according to d'), and then a stage f') that consists in drying said particles that are obtained according to e') before the implementation of said stage g') that is described above for the implementation of said second process for preparation of the material that is present in the catalyst according to the invention.

A third process for preparation of the crystalline material with hierarchized and organized porosity, called "third process for preparation of said material that is present in the catalyst according to the invention" below, comprises the stages: a") the redispersion in solution of zeolitic crystals so as to obtain a colloidal solution of zeolitic nanocrystals with a maximum nanometric size that is equal to 60 nm, b") the mixing in solution of at least one surfactant, at least said colloidal solution that is obtained according to a"), and at least one clear solution that contains the precursor elements of zeolitic entities, namely at least one structuring agent, at least one silicic precursor, and at least one precursor of at least one element X that is selected from among aluminum, iron, boron, germanium, and titanium, whereby X is advantageously aluminum, and whereby said mixture is such that the ratio of the volumes of inorganic and organic materials $V_{inorganic}/V_{organic}$ is between 0.26 and 4; c") atomization by aerosol of said solution that is obtained in stage b") for leading to the formation of spherical droplets; d") the drying of said droplets; e") the autoclaving of the particles that are obtained according to d"); f") the drying of said particles that are obtained according to e"); and g") the elimination of said structuring agent and said surfactant for obtaining a crystallized material with hierarchized and organized porosity in the fields of microporosity and mesoporosity.

The clear solution that contains the precursor elements of zeolitic entities prepared during stage a) of the first process for preparation of the material that is present in the catalyst according to the invention, stage b') of the second variant of the second process for preparation of the material that is present in the catalyst according to the invention, and stage b") of the third process for preparation of the material that is present in the catalyst according to the invention, and the colloidal solution that contains zeolitic nanocrystals with a maximum nanometric size that is equal to 60 nm, prepared during stages a') and a") respectively of the second and third processes for preparation of the material that is present in the catalyst according to the invention, are prepared starting from operating protocols that are known to one skilled in the art.

The silicic precursor that is used for the implementation of stages a), a') and b"), respectively of the first, second and third processes for preparation of the material that is present in the catalyst according to the invention as well as for the implementation of stage b') of the second variant of the second process for preparation of the material that is present in the catalyst according to the invention, is selected from among the silicon oxide precursors that are well known to one skilled in the art. In particular, a silicic precursor that is selected from among the silica precursors usually used in the synthesis of zeolites or related solids is advantageously used; for example, a solid silica in powder form, silicic acid, colloidal silica, dissolved silica or tetraethoxysilane that is also called tetraethylorthosilicate (TEOS) is used. In a preferred manner, the silicic precursor is TEOS.

The precursor of the element X, used for the implementation of stages a), a') and b"), respectively of the first, second and third processes for preparation of the material that is present in the catalyst according to the invention as well as for the implementation of stage b') of the second variant of the second process for preparation of the material that is present in the catalyst according to the invention, can be any compound that comprises the element X and that can release this element in solution, in particular into an aqueous solution or aquo-organic solution, in reactive form. In the advantageous case where X is aluminum, the aluminum precursor is advantageously an inorganic aluminum salt of formula $AlZ_3$, whereby Z is a halogen, a nitrate or an oxide. Preferably, Z is chlorine. The aluminum precursor can also be an aluminum sulfate of formula $Al_2(SO_4)_3$. The aluminum precursor can also be an organometallic precursor of formula $Al(OR)_3$, where R=ethyl, isopropyl, n-butyl, s-butyl ($Al(O^sC_4H_9)_3$) or t-butyl or a chelated precursor such as aluminum acetyl acetonate ($Al(C_5H_8O_2)_3$). Preferably, R is s-butyl. The aluminum precursor can also be sodium aluminate or ammonium aluminate or alumina itself in one of its crystalline phases that are known to one skilled in the art (alpha, delta, theta, gamma), preferably in hydrated form or that can be hydrated.

It is also possible to use mixtures of the precursors cited above. Some or all of the aluminum and silicic precursors can optionally be added in the form of a single compound that comprises both aluminum atoms and silicon atoms, for example an amorphous silica-alumina.

The structuring agent that is used for the implementation of stages a), a') and b") respectively of the first, second and third processes for preparation of the material that is present in the catalyst according to the invention as well as for the implementation of stage b') of the second variant of the second process for preparation of the material that is present in the catalyst according to the invention can be ionic or neutral according to the zeolite or the related solid to be synthesized. It is common to use structuring agents of the following non-exhaustive list: nitrogen-containing organic cations such as tetrapropylammonium (TPA), elements of the family of alkalines (Cs, K, Na, etc.), crown ethers, diamines, as well as any other structuring agent that is well known to one skilled in the art for the synthesis of zeolite.

The clear solution that contains precursor elements of zeolitic entities (stage a) of the first process for preparation of the material that is present in the catalyst according to the invention, stage b') of the second variant of the second process for preparation of the material that is present in the catalyst according to the invention, and stage b") of the third process for preparation of the material that is present in the catalyst according to the invention, as well as the colloidal solution (stage a') of the second process for preparation of the material that is present in the catalyst according to the invention, stage a") of the third process for preparation of the material that is present in the catalyst according to the invention) containing zeolitic nanocrystals, employed for the implementation of different stages of different processes for preparation of the material that is present in the catalyst according to the invention, are synthesized according to operating protocols that are known to one skilled in the art. In particular, clear solutions that contain precursor elements of beta-type zeolitic entities or colloidal solutions that contain beta-type zeolitic nanocrystals are produced from the operating protocol described by P. Prokesova, S. Mintova, J. Cejka, T. Bein et coll., *Micropor. Mesopor. Mater.*, 2003, 64, 165. Clear solutions that contain precursor elements of FAU-type zeolitic entities or colloidal solutions that contain FAU-type zeolitic nanocrystals are produced starting from operating protocols described by Y. Liu, W. Z. Zhang, T. J. Pinnavaia et coll., *J. Am. Chem. Soc.*, 2000, 122, 8791, and K. R. Kloetstra, H. W. Zandbergen, J. C. Jansen, H. van Bekkum, *Microporous Mater.* 1996, 6, 287. Clear solutions that contain precursor elements of ZSM-5-type zeolitic entities or colloidal solutions that contain ZSM-5-type zeolitic nanocrystals are made starting from the operating protocol described by A. E. Persson, B. J. Schoeman, J. Sterte, and J.-E. Otterstedt, *Zeolites*, 1995, 15, 611.

In general, the clear solution that contains the precursor elements of zeolitic entities is obtained according to stages a), b') and b") respectively of the first, second variants of the second and third processes for preparation of the material that is present in the catalyst according to the invention or else the colloidal solution, that contains zeolitic nanocrystals with a maximum nanometric size that is equal to 60 nm according to stage a') of the second process for preparation of the material that is present in the catalyst according to the invention by preparing a reaction mixture that contains at least one silicic precursor, at least one precursor of at least one element X that is selected from among aluminum, iron, boron, titanium and germanium, whereby X is advantageously aluminum, and at least one structuring agent. The reaction mixture is either aqueous or aquo-organic, for example a water-alcohol mixture.

According to stage a) of the first process for preparation of the material that is present in the catalyst according to the invention, the reaction mixture can be put under hydrothermal conditions under an autogenous pressure, optionally by adding a gas, for example nitrogen, at a temperature of between ambient temperature and 200° C., preferably between ambient temperature and 170° C., and in an even more preferred manner at a temperature that does not exceed 120° C. up to the formation of a clear solution that contains the precursor elements of the zeolitic entities, which constitute exclusively the crystallized walls of the matrix of each of the spherical particles of the material that is present in the catalyst according to the invention. According to a preferred operating mode, the reaction mixture that contains at least one structuring agent, at least one silicic precursor, and at least one precursor of at least one element X that is selected from among aluminum, iron, boron, titanium and germanium, whereby X is advantageously aluminum, is cured at ambient temperature for a period that is advantageously between 15 and 20 hours, so as to obtain a clear solution that contains the precursor elements of zeolitic entities that can generate the formation of crystallized zeolitic entities during the autoclaving stage e) of said first process for preparation of the material that is present in the catalyst according to the invention. The clear solution that contains precursors of zeolitic entities according to stage b') of the second variant of said second process for preparation of the material that is present in the catalyst according to the invention and that according to stage b") of said third process for preparation of the material that is present in the catalyst according to the invention are advantageously prepared in the same manner as said clear solution that contains precursors of zeolitic entities according to stage a) of said first process for preparation of the material that is present in the catalyst according to the invention.

According to stage a') of the second process for preparation of the material that is present in the catalyst according to the invention, the reaction mixture is advantageously put under hydrothermal conditions under an autogenous pressure, optionally by adding gas, for example nitrogen, at a temperature of between 50 and 200° C., preferably between 60 and 170° C., and in an even more preferred manner at a temperature of between 60 and 120° C. until zeolitic nanocrystals with a maximum nanometric size that is equal to 60 nm form. In a preferred manner, the reaction mixture is cured at a temperature of between 70° C. and 100° C. for a period of between 3 and 6 days. At the end of said hydrothermal treatment, a colloidal solution is obtained in which said nanocrystals are in the dispersed state. The synthesis of said zeolitic nanocrystals is followed by large-angle x-ray diffraction, and the size of said nanocrystals is monitored by diffusion of light and by Transmission Electron Microscopy. One skilled in the art will know to adjust the operating conditions so as to obtain said colloidal solution in which said nanocrystals, with a maximum nanometric size that is equal to 60 nm are in the dispersed state.

It is preferred to work in a basic reaction medium during various stages of the first and second processes for preparation of the material that is present in the catalyst according to the invention so as to promote the development of the zeolitic entities that constitute the crystallized walls of the matrix of each of the particles of the material that is present in the catalyst according to the invention. The basicity of the clear solution according to stage a) of said first process for preparation or of the colloidal solution according to stage a') of said second process for preparation or of the clear solution according to stage b') of the second variant of said second process for preparation of the material that is present in the catalyst according to the invention is advantageously ensured by the basicity of the structuring agent that is used or else by basification of the reaction mixture by adding a basic compound, for example an alkaline metal hydroxide, preferably sodium hydroxide, in stage a), a') or b'), b").

According to stage a") of the third process for preparation of the material that is present in the catalyst according to the invention, zeolitic crystals are used. Said zeolitic crystals can have a size that ranges beyond 60 nm. Any crystallized zeolite or related solid that develops acidicity properties known in the prior art that has the property of dispersing in solution, for example by aquo-organic solution, in the form of nano-cyrstals with a maximum nanometric size that is equal to 60 nm, is suitable for the implementation of stage a"). The dispersion of said zeolitic crystals is implemented by any method that is known to one skilled in the art, for example by sonication. Said zeolitic crystals are synthesized by methods that are known to one skilled in the art. The zeolitic crystals that are used in stage a") can already be in the form of nanocrystals. Obtaining zeolitic crystals that disperse in the form of nanocrystals with a maximum nanometric size that is equal to 60 nm is also possible by producing a functionalization of the surface of nanocrystals. The zeolitic crystals that are used are either in their crude synthesis form, i.e., also containing structuring agent, or in their calcined form, i.e., said structuring agent is removed therefrom. When the zeolitic crystals that are used are in their crude synthesis form, said structuring agent is eliminated during stage g") from the third process for preparation of the material that is present in the catalyst according to the invention.

According to stage b), stage b') and stage b") respectively of the first, second and third processes for preparation of the material that is present in the catalyst according to the invention, the surfactant that is used is an ionic or non-ionic surfactant or a mixture of the two; preferably the surfactant that is used is a non-ionic surfactant. Preferably, the ionic surfactant is selected from among the anionic surfactants such as the sulfates, such as, for example, sodium dodecyl sulfate (SDS). Preferably, the non-ionic surfactant can be any copolymer that has at least two parts of different polarities that impart to them properties of amphiphilic macromolecules. These copolymers can comprise at least one block that is part of the non-exhaustive list of the families of the following polymers: the fluorinated polymers ($—[CH_2—CH_2—CH_2—CH_2—O—CO—R1-$ with $R1=C_4F_9$, $C_8C_{17}$, etc.), the biological polymers such as amino polyacids (poly-lysine, alginates, etc.), the dendrimers, and the polymers that consist of chains of poly(alkylene oxide). Any other copolymer that is amphiphilic in nature and that is known to one skilled in the art can be used if it makes it possible to obtain a stable solution, i.e., clear or colloidal, in the stages b), b') and b") respectively of the first, second and third processes for preparation of the material that is present in the catalyst according to the invention, such as poly(styrene-b-acrylamide) for example (S. Förster, M. Antionnetti, *Adv. Mater.*, 1998, 10, 195; S. Förster, T. Plantenberg, *Angew. Chem. Int. Ed*, 2002, 41, 688; H. Cölfen, *Macromol. Rapid Commun*, 2001, 22, 219). In a preferred manner, within the scope of this invention, a block copolymer that consists of a poly(alkylene oxide) chain is used. Said block copolymer is preferably a block copolymer that has two, three or four blocks, each block consisting of a poly(alkylene oxide) chain. For a two-block copolymer, one of the blocks consists of a poly(alkylene oxide) chain that is hydrophilic in nature, and the other block consists of a poly(alkylene oxide) chain that is hydrophobic in nature. For a three-block copolymer, at least one of the blocks consists of a chain of poly(alkylene oxide) that is hydrophilic in nature, while at least one of the other blocks consists of a poly(alkylene oxide) chain that is hydrophobic in nature. Preferably, in the case of a three-block copolymer, the poly (alkylene oxide) chains that are hydrophilic in nature are poly(ethylene oxide) chains that are denoted $(PEO)_x$ and $(PEO)_z$, and the poly(alkylene oxide) chains that are hydrophobic in nature are poly(propylene oxide) chains denoted $(PPO)_y$, poly(butylene oxide) chains, or mixed chains of which each chain is a mixture of several alkylene oxide monomers. In a very preferred manner, in the case of a three-block copolymer, the latter consist of two poly(ethylene oxide) chains and a poly(propylene oxide) chain. More precisely, a compound of formula $(PEO)_x-(PPO)_y-(PEO)_z$ is used, where x is between 5 and 300, and y is between 33 and 300, and z is between 5 and 300. Preferably, the values of x and z are identical. Very advantageously, a compound in which x=20, y=70, and z=20 (P123) is used, and a compound in which x=106, y=70, and z=106 (F127) is used. The commercial non-ionic surfactants that are known under the name of Pluronic (BASF), Tetronic (BASF), Triton (Sigma), Tergitol (Union Carbide), and Brij (Aldrich) can be used as non-ionic surfactants in the stages b), b') and b") respectively of the first, second and third processes for preparation of the material that is present in the catalyst according to the invention. For a four-block copolymer, two of the blocks consist of a poly (alkylene oxide) chain that is hydrophilic in nature, and the two other blocks consist of a poly(alkylene oxide) chain that is hydrophobic in nature.

The solution that is obtained at the end of stages b), b') and b") respectively of the first, second and third processes for preparation of the material that is present in the catalyst according to the invention can be acidic, neutral or basic. Preferably, said solution is basic and preferably has a pH that is greater than 9, whereby this value of the pH is generally imposed by the pH of the clear solution that contains the precursor elements of zeolitic entities according to stage a) of the first process for preparation of the material that is present in the catalyst according to the invention or else the colloidal solution that contains zeolitic nanocrystals with a maximum nanometric size that is equal to 60 nm according to stages a') and a") respectively of said second and third processes for preparation of the material that is present in the catalyst according to the invention. The solution that is obtained at the end of stages b), b') and b") can be aqueous or can be an organic water-solvent mixture, whereby the organic solvent is preferably a polar solvent, in particular an alcohol, preferably ethanol.

The quantity of organic compounds, i.e., of surfactant and of structuring agent, present in the mixture according to stages b), b') and b") respectively of the first, second and third processes for preparation of the material that is present in the catalyst according to the invention, is defined relative to the quantity of inorganic material that is present in said mixture following the addition of the clear solution that contains the precursor elements of zeolitic entities according to stage a) of the first process for preparation of the material that is present in the catalyst according to the invention or else following the addition of the colloidal solution that contains zeolitic nanocrystals with a maximum nanometric size that is equal to 60 nm according to stage a') of the second process for preparation of the material that is present in the catalyst according to the invention, and optionally the addition of the clear solution according to stage b') if the material that is present in the catalyst according to the invention is prepared according to the second variant of said second process for preparation, or else even following the addition of the colloidal solution that contains zeolitic nanocrystals with a maximum nanometric size that is equal to 60 nm according to stage a"), and the clear solution that is introduced in stage b") of the third process for preparation of the material that is present in the catalyst according to the invention. The quantity of inorganic material corresponds to the quantity of material of the silicic precursor and to that of the precursor of the element X. The volumetric ratio $V_{inorganic}/V_{organic}$ is such that the binary organic-inorganic system that is formed during atomization stages c), c') and c") respectively of the first, second and third processes for preparation of the material that is present in the catalyst according to the invention undergoes a process for mesostructuring by self-assembly of the surfactant together with the hydrolysis/condensation reactions of the various inorganic precursors. Said volumetric ratio $V_{inorganic}/V_{organic}$ is defined as follows: $V_{inorganic}/V_{organic}=(m_{inorg}*\rho_{org})/(m_{org}*\rho_{inorg})$, where $m_{inorg}$ is the final mass of the inorganic fraction in the form of condensed oxide(s) in the solid elementary particle obtained by atomization; $m_{org}$ is the total mass of the non-volatile organic fraction that is in the solid elementary particle that is obtained by atomization; $\rho_{org}$ and $\rho_{inorg}$ are the densities that are respectively combined with non-volatile organic and inorganic fractions. Within the scope of the invention, when the element X is aluminum and for a simplification of the calculations (approximations that are valid for a large majority of the non-volatile organic fraction and for an inorganic fraction of the "aluminosilicate network" type), it is considered that $\rho_{org}=1$, and $\rho_{inorg}=2$. Within the scope of the invention, $m_{inorg}$ generally corresponds to the mass of $SiO_2$ that is added to that of the mass of $AlO_2$, when X is aluminum, and $m_{org}$ corresponds to the mass of the structuring agent, for example TPAOH, added to the mass of the surfactant, for example, the surfactant F127. The polar solvent, preferably ethanol, as well as water and soda, are not taken into account in the calculation of said $V_{inorganic}/V_{organic}$ ratio. The radicals that comprise an element X, advantageously the alumina radicals, introduced after the implementation of said stage b), b') or b"), respectively of the first, second or third processes for preparation of the material that is present in the catalyst, are not taken into account for the calculation of the volumetric ratio $V_{inorganic}/V_{organic}$ defined above. According to the invention, the quantity of organic material and the quantity of inorganic material in the mixture that is obtained after the implementation of stage b), b') and b"), respectively of the first, second and third processes for preparation of the material that is present in the catalyst according to the invention, is such that the ratio $V_{inorganic}/V_{organic}$ is encompassed in a range of 0.26 to 4, preferably in a range of 0.3 to 2. According to stages b), b') and b") respectively of the first, second and third processes for preparation of the material that is present in the catalyst according to the invention, the initial concentration of surfactant, introduced into the mixture, defined by $c_o$, is such that $c_o$ is less than or equal to $c_{mc}$, with the parameter $c_{mc}$ representing the critical micellar connection that is well known to one skilled in the art, e.g., the boundary concentration beyond which the self-assembly phenomenon of the molecules of the surfactant occurs in the solution that is obtained at the end of stages b), b') and b") respectively of the first, second and third processes for preparation of the material that is present in the catalyst according to the invention. Before atomization, the concentration of surfactant molecules of the solution obtained at the end of stages b), b') and b") respectively of the first, second and third processes for preparation of the material that is present in the catalyst according to the invention therefore does not lead to the formation of particular micellar phases. In one preferred implementation of the different processes for preparation according to the invention, the concentration $c_o$ is less than the $c_{mc}$, the ratio $V_{inorganic}/V_{organic}$ is such that the composition of the binary system verifies the conditions of composition for which a mesostructuring mechanism is produced by cooperative self-assembly of the reagents ($V_{inorganic}/V_{organic}$ between 0.26 and 4, preferably between 0.3 and 2), and said solution that is targeted at stages b), b') and b") respectively of the first, second and third processes for preparation of the material that is present in the catalyst according to the invention is a basic water/alcohol mixture.

The stage for atomization of the mixture according to stages c), c') and c") respectively of the first, second and third processes for preparation of the material that is present in the catalyst according to the invention produces spherical droplets. The size distribution of these droplets is lognormal. The aerosol generator that is used here is a commercial device of model 9306 A provided by TSI and having a 6-jet atomizer. The atomization of the solution is done in a chamber in which a carrier gas, a mixture of $O_2/N_2$ (dry air), is sent under a pressure P that is equal to 1.5 bar.

According to stages d), d') and d") respectively of the first, second and third processes for preparation of the material that is present in the catalyst according to the invention, the drying of said droplets is initiated. This drying is implemented by the transport of said droplets via the carrier gas, the $O_2/N_2$ mixture, in PVC pipes, which leads to the gradual evaporation of the solution, for example the aquo-organic solution, preferably the basic aquo-organic solution, obtained during stages b), b') and b") respectively of the first, second and third processes for preparation of the material that is present in the catalyst according to the invention, and thus to obtaining spherical elementary particles. This drying is completed by running said particles into a furnace whose temperature can be adjusted, the conventional temperature range varying from 50 to 600° C. and preferably from 80 to 400° C., whereby the dwell time of these particles in the furnace is on the order of a second. The particles are then collected in a filter. A pump that is placed at the circuit's end helps channel the radicals into the experimental aerosol device. The drying of the droplets according to stages d), d') and d"), respectively of the first, second and third processes for preparation of the material that is present in the catalyst according to the invention, is advantageously followed by being run through the oven at a temperature of between 50 and 150° C.

According to stages e), e') and e") of the first variants of the second and third processes for preparation of the material that is present in the catalyst according to the invention, it is possible to initiate autoclaving of the dried particles that are obtained at the end of stages d), d') and d") of the three different processes for preparation of the material that is present in the catalyst according to the invention in the presence of a solvent. This stage consists in placing said particles in a closed chamber in the presence of a solvent at a given temperature so as to work with autogenous pressure that is associated with the selected operating conditions. The solvent that is used is advantageously a protic polar solvent. Preferably, the solvent that is used is water. The volume of solvent that is introduced is defined relative to the volume of the selected autoclave, the mass of dry powder that is introduced, and the treatment temperature. Thus, the volume of solvent that is introduced is encompassed in a range of 0.01 to 20% relative to the volume of the selected autoclave, preferably in a range of 0.05 to 5%, and more preferably in a range of 0.05 to 1%. The autoclaving temperature is between 50 and 200° C., preferably between 60 and 170° C., and in an even more preferred manner between 60 and 120° C. so as to allow the growth of zeolitic entities in the walls of the matrix of each of the particles of the material that is present in the catalyst according to the invention without generating zeolite crystals that are too large that would disrupt the mesostructuring of each particle of the material that is present in the catalyst according to the invention. The autoclaving is maintained over a period of 1 to 196 hours and preferably over a period of 10 to 72 hours.

According to stages f), f') and f") respectively of the first variants of the second and third processes for preparation of the material that is present in the catalyst according to the invention, the drying of the particles after autoclaving is advantageously done by stoving at a temperature of between 50 and 150° C.

In the case where the element X is advantageously aluminum and where the sodium element is present in the solution that is obtained according to stages a), a'), b') and b") respectively of the first, second, second [sic] variant of the second and third processes for preparation of the material that is present in the catalyst according to the invention via the use of sodium hydroxide and/or a soda structuring agent that ensures the basicity of said solution or else is present in the crystals of precursor zeolites of stage a") of the third process for preparation of the material that is present in the catalyst according to the invention, it is preferred to implement an additional stage of ionic exchange that makes it possible to exchange the $Na^+$ cation by the $NH_4^+$ cation between the stages f) and g) if the material that is present in the catalyst according to the invention is prepared according to said first preparation process, between the stages f') and g') if the material that is present in the catalyst according to the invention is prepared according to the second preparation process, between the stages f') and g') if the material that is present in the catalyst according to the invention is prepared according to one of the variants of said second preparation process, between the stages f") and g") if the material that is present in the catalyst according to the invention is prepared according to said third preparation process. This exchange, which leads to the formation of $H^+$ protons after the stages g), g') and g") respectively of the first, second and third processes for preparation of the material that is present in the catalyst according to the invention in the preferred case where the elimination of the structuring agent and of the surfactant is implemented by calcination in air, is implemented according to operating protocols that are well known to one skilled in the art. One of the conventional methods consists in suspending the dried solid particles that are obtained from stages f), d') and f") respectively of the first, second and third processes for preparation of the material that is present in the catalyst according to the invention and stage f') of one of the variants of the second process for preparation of the material that is present in the catalyst according to the invention if it is made in an aqueous solution of ammonium nitrate. The mass is then brought to reflux for a period of 1 to 6 hours. The particles are then recovered by filtration (centrifuging at 9,000 rpm), washed and then dried by running through the oven at a temperature of between 50 and 150° C. This ion exchange/washing/drying cycle can be conducted several times and preferably two other times. This exchange cycle can also be implemented after the stages f) and g) of said first preparation process, after the stages d') and g') of said second preparation process, after the stages f') and g') of one of the variants of said second preparation process, and after the stages f") and g") of said third preparation process. Under these conditions, the stages g), g') and g") respectively of the first, second and third processes for preparation of the material that is present in the catalyst according to the invention are then reproduced after the last exchange cycle so as to generate the $H^+$ protons as explained above.

According to stages g), g') and g") respectively of the first, second and third processes for preparation of the material that is present in the catalyst according to the invention, the elimination of the structuring agent and the surfactant so as to obtain the crystallized material according to the invention with hierarchized and organized porosity in the fields of microporosity and mesoporosity is advantageously implemented by processes for chemical extraction or by heat treatment and preferably by calcination in air in a temperature range of 300 to 1,000° C. and more specifically in a range of 400 to 600° C. for a period of 1 to 24 hours and preferably for a period of 2 to 12 hours.

In the case where the solution targeted in stages b), b') and b") respectively of the first, second and third processes for preparation of the material that is present in the catalyst according to the invention is a water-organic solvent mixture, preferably basic, it is essential during said stages b), b') and b") that the concentration in surfactant at the origin of the mesostructuring of the matrix is less than the critical micellar concentration and that the ratio $V_{inorganic}/V_{organic}$ is between 0.26 and 4, preferably between 0.3 and 2, such that the evaporation of said aquo-organic solution, preferably basic, during stages c), c') and c") respectively of the first, second and third processes for preparation, of the material that is present in the catalyst according to the invention by the aerosol technique induces a phenomenon of micellization or self-assembly leading to the mesostructuring of the matrix of the material that is present in the catalyst according to the invention. When $c_o<c_{mc}$, the mesostructuring of the matrix of the material that is present in the catalyst according to the invention follows a gradual concentration, within each droplet, of the precursor elements of zeolitic entities of the clear solution that is obtained in stage a) of the first process for preparation of the material that is present in the catalyst according to the invention or else zeolitic nanocrystals of the colloidal solution that is obtained in stage a') of said second preparation process, or else zeolitic nanocrystals of the colloidal solution that is obtained in stage a') and precursor elements of zeolitic entities of the clear solution that is obtained in stage b') of the second variant of said second preparation process or else even zeolitic nanocrystals of the colloidal solution that is obtained in stage a") and precursor elements of zeolitic entities of the clear solution that is obtained in stage b") of said third preparation process and at least one surfactant that is introduced during stages b), b') and b") of the three processes for preparation of the material that is present in the catalyst according to the invention, up to a surfactant concentration $c>c_{mc}$ that results from an evaporation of the aquo-organic solution.

According to a first preferred embodiment of each of the three processes for preparation of the material that is present in the catalyst according to the invention, at least one precursor of at least one element X that is selected from among aluminum, iron, boron, germanium and titanium, whereby X is advantageously aluminum, is introduced for the implementation of stage b) of the first process for preparation of the material that is present in the catalyst according to the invention, of stage b') of the second process for preparation of the material that is present in the catalyst according to the invention, of stage b') of one of the variants of said second process for preparation of the material that is present in the catalyst according to the invention, or of stage b") of said third process for preparation of the material that is present in the catalyst according to the invention. Thus, the mixing in solution of at least one surfactant and at least said clear solution that is obtained according to stage a) of the first process for preparation of the material that is present in the catalyst according to the invention or at least one surfactant and at least said colloidal solution that is obtained according to stage a') of the second process for preparation of the material that is present in the catalyst according to the invention, or at least one surfactant, of at least said colloidal solution that is obtained according to stage a') and at least said clear solution that is obtained according to stage b') of the second variant of said second preparation process, or else at least one surfactant, of at least said colloidal solution that is obtained according to stage a") and at least said clear solution that is obtained according to stage b") of said third preparation process, is implemented in the presence of at least one precursor of said element X that is selected from among aluminum, iron, boron, germanium and titanium, whereby X is advantageously aluminum, preferably from among the aluminum precursors, described above in this description, for example for the implementation of said stage a) of said first process for the preparation of the material that is present in the catalyst according to the invention. According to said first preferred embodiment of each of the three processes for preparation of the material that is present in the catalyst according to the invention, the preparation of the clear solution according to stage a), stage b') or stage b") respectively of the first, second variant of the second or third process for preparation of the material that is present in the catalyst according to the invention and that of the colloidal solution according to stage a') of said second preparation process is implemented either in the presence or in the absence of at least one precursor of at least one element X.

According to a second preferred embodiment of each of the three processes for preparation of the material that is present in the catalyst according to the invention, at least one precursor of at least one element X that is selected from among aluminum, iron, boron, germanium and titanium, whereby X is advantageously aluminum, is introduced either during the implementation of said stage d) and/or said stage f) and/or said g) of said first process for preparation of the material that is present in the catalyst according to the invention, or during the implementation of said stage d') and/or said stage of said second process for the preparation of the material that is present in the catalyst according to the invention, or during the implementation of said stage d') and/or said stage f') and/or said stage g') of one of the variants of said second preparation process or else during the implementation of said stage d") and/or said stage f") and/or said stage g") of said third preparation process, for the purpose of producing a surface modification of the material that is present in the catalyst according to the invention. According to said second preferred embodiment of each of the three processes for preparation of the material that is present in the catalyst according to the invention, said precursor of at least one element X that is selected from among aluminum, iron, boron, germanium and titanium, whereby X is advantageously aluminum, is introduced during the implementation of at least one of the stages cited above (d, d', d", f, f', f", g, g', and g") by any surface modification technique that is well known to one skilled in the art, such as the grafting of at least one precursor of at least one element X, dry impregnation of at least one precursor of at least one element X, and excess impregnation of at least one precursor of at least one element X. Said precursor of at least one element X, advantageously an aluminum precursor, introduced during the implementation of at least one of the stages cited above (d, d', d", f, f', f", g, g' and g") by a surface modification technique, is selected from among the precursors of said element X, advantageously from among the aluminum precursors, described above in this description, for example those used for the implementation of said stage a) of said first process for preparation of the material that is present in the catalyst according to the invention. According to said second preferred embodiment of each of the three processes for preparation of the material that is present in the catalyst according to the invention, stage a) and stage a') of the first and second processes for preparation of the invention are implemented in the presence or in the absence of at least one precursor of at least one element X, advantageously an aluminum precursor, and stage b), stage b') or stage b") respectively of the first, second or third process for preparation of the material that is present in the catalyst according to the invention is implemented in the presence or in the absence of at least one precursor of at least one element X, advantageously an aluminum precursor.

According to the three processes for preparation of the material that is present in the catalyst according to the invention, said first preferred embodiment of each of the three processes for preparation of the material that is present in the catalyst according to the invention and said second preferred embodiment of each of the three processes for preparation of the material that is present in the catalyst according to the invention are only optional variants of each of the three processes for preparation of the material that is present in the catalyst according to the invention. Also, the element X, advantageously aluminum, is introduced, when the material is prepared according to the first process for preparation of the material that is present in the catalyst according to the invention, either during said stage a) of the first process for preparation of the material that is present in the catalyst according to the invention for the preparation of said clear solution, or during said stage b) according to said first preferred embodiment of the first process for preparation of the material that is present in the catalyst according to the invention, or else during said stage d) and/or said stage f) and/or said stage g) according to said second preferred embodiment of the first process for preparation of the material that is present in the catalyst according to the invention. When the material is prepared according to said second process for preparation of the material that is present in the catalyst according to the invention, said element X, advantageously aluminum, is introduced either during said stage a') or during said stage b') according to said first preferred embodiment of the second process for preparation of the material that is present in the catalyst according to the invention or else during said stage d') and/or said stage f') and/or stage g') according to said second preferred embodiment. When the material is prepared according to said second variant of said second process for preparation of the material that is present in the catalyst according to the invention, said element X, advantageously aluminum, is introduced either during said stage a') or during stage b') for the preparation of said clear solution, or during said stage b') according to said first preferred embodiment or else during said stage d') and/or stage f') and/or stage g') according to said second preferred embodiment. When the material is prepared according to said third process for preparation of the material that is present in the catalyst according to the invention, the element X, advantageously aluminum, is introduced either during said stage b") for the preparation of said clear solution, or during said stage b") according to said first preferred embodiment, or else during said stage d") and/or stage f") and/or stage g") according to said second preferred embodiment. The element X, advantageously aluminum, can also be introduced, several times, during the implementation of several stages according to all of the possible combinations of the embodiments described above.

In particular, it is advantageous to introduce aluminum during said stage a) and said stage b) or during said stage a) and said stage d) and/or said stage e) when the material that is present in the catalyst according to the invention is prepared according to said first process for preparation of the material that is present in the catalyst according to the invention.

In the case where the element X is advantageously aluminum, crystallized aluminosilicate, obtained according to one of the thee processes for preparation of the material that is present in the catalyst according to the invention, then has an Si/Al molar ratio that is defined starting from the quantity of silicon element that is introduced during stages a), a'), a"), b') and b") respectively of the first, second, third, second variant of the second and third processes for preparation of the material that is present in the catalyst according to the invention and the total quantity of the aluminum element introduced in the stage(s) of one of the three processes for preparation according to the different preferred embodiments described above. Under these conditions and in a preferred manner, the range of the Si/Al molar ratio of the crystallized material according to the invention is between 0.5 and 1,000.

When said first preferred embodiment of each of the three processes for preparation of the material that is present in the catalyst according to the invention is applied, the quantities of organic and inorganic material to be introduced for the implementation of stage b), stage b') and/or stage b") are to be adjusted based on the quantity of additional material of element X, advantageously of aluminum, introduced into said stage b), b') or b") according to said first method so that the total quantity of organic and inorganic material that is introduced for the preparation of the material according to the invention made possible a phenomenon of micellization that leads to the mesostructuring of the matrix of each particle of said material. The element X, advantageously aluminum, introduced for the implementation of said second preferred embodiment of each of the three processes for preparation of the material that is present in the catalyst according to the invention, does not play a role in the calculation of the ratio $V_{inorganic}/V_{organic}$ as defined above in this description since it is introduced after the stage that makes possible a micellization phenomenon that leads to the mesostructuring of the matrix of each particle of said material that is present in the catalyst according to the invention.

It is specified that in the entire text of the description of this invention, the expression "second process for preparation of the material that is present in the catalyst according to the invention" also duly applies in the case where the material that is present in the catalyst according to the invention is prepared according to the second process for preparation of the material that is present in the catalyst according to the invention (without applying either of the two variants), in the case where the material that is present in the catalyst according to the invention is prepared according to the first variant of said second process for preparation of the material that is present in the catalyst according to the invention, as well as in the case where the material that is present in the catalyst according to the invention is prepared according to the second variant of said second process for preparation of the material that is present in the catalyst according to the invention.

The crystallized material with hierarchized and organized porosity in the fields of microporosity and mesoporosity present in the catalyst according to the invention is obtained in powder form, which consists of elementary spherical particles that have a maximum diameter of 200 μm.

The preparation of the catalyst according to the invention comprises a stage for shaping the crystallized material with hierarchized and organized porosity, whereby said material is prepared according to one of three preparation processes described above in this description, with at least one binder that is selected from among the binders that are described above, preferably an aluminum binder. The shaping can be implemented, for example, by extrusion, by pelletizing, by the drop (oil-drop) coagulation method, by the rotating groove or drum method, by turntable granulation, or by any other method that is well known to one skilled in the art. In a preferred manner, the catalyst according to the invention comes in the form of cylindrical or multilobed extrudates such as bilobed, trilobed, or multilobed extrudates of straight or twisted shape, but can also optionally come in the form of crushed powders, tablets, rings, balls, and wheels. The shaping conditions of the catalyst, the selection of binder, optionally the preliminary grinding of material, the peptization process, the addition of pore-forming agents, the mixing time, the extrusion pressure if the catalyst according to the invention is put in the form of extrudates, and the speed and time of drying are determined for each binder according to the well-known rules of one skilled in the art. In particular, for a shaping by extrusion, the latter is advantageously implemented by any conventional tool that is available commercially. The paste that is obtained from mixing is advantageously extruded through a die, for example using a piston or a single- or double-extrusion screw. This extrusion stage is advantageously implemented by any method that is known to one skilled in the art. In a very preferred manner, the catalyst according to the invention comes in the form of extrudates with a diameter of between 0.5 and 5 mm, and more particularly between 0.7 and 2.5 mm. In a preferred manner, the cylindrical shapes are used.

After shaping, the catalyst is subjected to a thermal post-treatment stage, preferably a calcination stage, which is advantageously implemented in air at a temperature of at least 150° C., preferably at least 250° C., and in a preferred manner between approximately 350° C. and 1,000° C.

The stage for shaping the catalyst according to the invention is preferably preceded by a stage for bringing said material with hierarchized and organized porosity, prepared according to one of the three preparation processes described above, into contact with at least said binder. Said contact advantageously takes the form of powder, ground powder, a suspension, or a suspension that has undergone a deagglomeration treatment. Thus, for example, the material with hierarchized and organized porosity can be put into a suspension that may or may not be slightly acidic, at a concentration that is adjusted to the final content of crystallized material with hierarchized and organized porosity that is targeted in the catalyst according to the invention. This suspension that is commonly called a slip is then mixed with the binder. This stage is implemented by any technique that is known to one skilled in the art.

The shaping of the catalyst according to the invention is preferably implemented starting from the crystallized material with hierarchized and organized porosity that is obtained at the end of stage g), g') or g") according to the preparation method of said material that is used. However, said shaping can also be implemented starting from a crystallized material with hierarchized and organized porosity that is obtained at the end of stage f), e'), f') or f") according to the preparation method of said material that is used since the heat treatment stage, subsequent to the shaping stage, ensures the elimination of said structuring agent and of said surfactant that are used for the preparation of said crystallized material with hierarchized and organized porosity in the fields of microporosity and mesoporosity.

According to the invention and according to a preferred embodiment for preparation of the catalyst according to the invention, the crystallized material with hierarchized and organized porosity, prepared according to one of the three processes for preparation described above in this description, is subjected to at least one chemical treatment that is selected from among a treatment for bringing said material into contact with at least one metal, a treatment by dealuminification and a treatment for neutralization of the acidity of the non-microporous surface of said material. The treatment by dealuminification and the treatment by neutralization of the acidity of the non-microporous surface of said material are preferably implemented on the material that is not shaped with a binder. The chemical treatment that consists in bringing said material into contact with at least one metal can be implemented either before or after the shaping of the catalyst according to the invention.

A first chemical treatment to which said crystallized material with hierarchized and organized porosity is advantageously subjected is the bringing into contact of said material with at least one metal. According to the content of alkaline metal(s)/alkaline-earths of the zeolitic entities that are present in said crystallized material with hierarchized and organized porosity, one or more ion exchange(s) are advantageously initiated in such a way that said zeolitic entities comprise between 70 and 100%, preferably between 80 and 100%, and in a very preferred manner between 85 and 100% of compensation cations of H+ protonic form, whereby the remaining cations are selected in a preferred manner from among the metals of groups IA and IIA of the periodic table, and more particularly said cation is selected from among the cations $Na^+$, $Li^+$, $K^+$, $Rb^+$, $Cs^+$, $Ba^{2+}$, and $Ca^{2+}$. The introduction of at least one metal that is selected from among the metals of groups JIB, VIIB and VIII is also advantageously initiated. The introduction of one or more metal(s), in particular in cationic form, is implemented by any technique that is known to one skilled in the art such as, for example, ion exchange, dry impregnation, excess impregnation, vapor phase deposition, etc. In a preferred manner, the introduction of one or more metal(s) is implemented by ion exchange(s). The ion exchange is generally implemented with a solution that contains a salt of the desired metal cation, in a manner known to one skilled in the art. The content by weight of metal(s) is advantageously between 0.01 and 10% by weight, and preferably between 0.05 and 5% by weight relative to the weight of the crystallized material with hierarchized and organized porosity.

A second chemical treatment to which said crystallized material with hierarchized and organized porosity that is present in the catalyst according to the invention is advantageously subjected is a dealuminification treatment when the element X is aluminum. Said dealuminification treatment makes it possible to vary the porosity and the Si/Al ratio of said material. In a preferred manner, the dealuminification treatment is implemented before the shaping of the catalyst according to the invention. A first method for so-called dealuminification by direct acid attack comprises a treatment by an aqueous solution of a mineral acid such as, for example, $HNO_3$ or HCl or an organic acid such as $CH_3CO_2H$. This stage can advantageously be repeated as many times as it is necessary so as to obtain the desired level of dealuminification. To reach the desired Si/Al ratio, it is necessary to select the operating conditions properly; from this standpoint, the most critical parameters are the temperature for treatment by the aqueous acid solution, the concentration of said acid, the nature of said acid, the ratio between the quantity of acid solution and the mass of treated material, the period of treatment and the number of treatments implemented. A second so-called heat treatment dealuminification method combined with an acid attack comprises at least one dealuminification cycle that comprises at least one heat treatment that is implemented, optionally and preferably in the presence of water vapor, at a temperature that is generally between 250 and 700° C. and followed by at least one acid attack by an aqueous solution of a mineral or organic acid. The heat treatment conditions, preferably implemented in the presence of water vapor (temperature, water vapor pressure and period of treatment), as well as the conditions of heat post-treatment acid attack (period of the attack, concentration of the acid, nature of the acid that is used, and the ratio between the volume of acid and the mass of material, number of treatments), are adapted so as to obtain the desired dealuminification level. The dealuminification cycle, comprising at least one heat treatment stage, preferably implemented in the presence of water vapor, and at least one stage of acid medium attack can advantageously be repeated as many times as it is necessary for obtaining a catalyst that has the desired characteristics.

A third chemical treatment to which said crystallized material with hierarchized and organized porosity is advantageously subjected is a treatment for neutralization of the acidity of the non-microporous surface of said crystallized material with hierarchized and organized porosity that is present in the catalyst according to the invention. This treatment is also called selecting treatment. The partial neutralization of the acidity can be done by any method that is known by one skilled in the art. The conventional method that is generally used to implement the specific selecting of the acid sites of a non-microporous surface is the adsorption of molecules whose kinetic diameter is greater than the diameter of the opening of the micropores of the crystallized material that is present in the catalyst according to the invention. The molecules that are generally used for passivating or selecting the non-microporous surface of the crystallized material that is present in the catalyst according to the invention are compounds that contain atoms that can interact with the sites of the non-microporous surface of the catalyst. In a preferred manner, the molecules that are used are organic or inorganic molecules that contain one or more silicon atom(s). In a very preferred manner, a molecular compound is involved that contains at least one silicon atom that is selected from among the compounds of formulas $Si-R_4$ and $Si_2-R_6$ where R can be either hydrogen, or an alkyl, aryl or acyl group, or an alkoxy (—OR') group, or a hydroxyl (—OH) group, or else a halogen, preferably an alkoxy (—OR') group. Within the same molecule $Si-R_4$ or $Si_t-R_6$, the group R can be either identical or different. For example, according to the formulas described above, it is possible to select molecular compounds with the formula $Si_2H_6$ or $Si(C_2H_5)_3(CH_3)$. Thus, the molecular compound that contains at least one silicon atom can be a compound such as silane, disilane, alkylsilane, alkoxysilane or siloxane. In a very preferred manner, said molecular compound has a composition of general formula $Si-(OR')_4$ where R is an alkyl, aryl or acyl group, preferably an alkyl group, and in a very preferred manner, an ethyl group. The implementation of said treatment for neutralization of the acidity of the non-microporous surface of the crystallized material that is present in the catalyst according to the invention is implemented by initiating the selecting of the non-microporous surface of the crystallized material with hierarchized and organized porosity by gas phase deposition called CVD ("Chemical Vapor Deposition") deposition or a liquid phase deposition called CLD ("Chemical Liquid Deposition") deposition by any of the methods that are known to one skilled in the art. The selecting stage can be followed by a heat treatment that is implemented at a temperature that is preferably between 250 and 700° C., and preferably between 300 and 600° C. Said heat treatment stage is implemented in air, in oxygen, in hydrogen, in nitrogen or in argon, or in a mixture of nitrogen and argon, whereby said stage optionally can be implemented in the presence of water vapor. The period of this treatment is advantageously between 2 and 5 hours.

The crystallized material in the catalyst according to the invention or the catalyst itself, after shaping, is subjected to said first chemical treatment and/or to said second chemical treatment and/or to said third chemical treatment. In a preferred manner, said crystallized material in the catalyst according to the invention or the catalyst itself, subjected to one or the other of said chemical treatments, is subjected to a heat treatment stage, preferably a calcination, preferably implemented in air at a temperature of at least 150° C., preferably at least 250° C., and in a more preferred manner between approximately 350° C. and 1,000° C.

Another object of the invention is a process for oligomerization of an olefinic feedstock that contains hydrocarbon molecules that have 2 to 12 carbon atoms per molecule in the presence of the catalyst according to the invention. In a preferred manner, the feedstock that is used for the implementation of said oligomerization process contains hydrocarbon molecules that contain 2 to 8 carbon atoms per molecule. The feedstock that is used in the oligomerization process according to the invention contains 20% to 100% by weight, and preferably from 25% to 80% by weight of olefins.

Possible sources for the olefinic feedstock used in the oligomerization process according to the invention are the light fraction obtained from catalytic cracking in a fluidized bed (fluid catalytic cracking, FCC) and/or a fraction that is obtained from a steam-cracking unit, and/or a fraction that is obtained from a unit for dehydrogenation of paraffins, and/or a unit for polymerizing dehydration of methanol in water and light olefins and/or other light fractions that contain olefins that are obtained from conversion units.

Said oligomerization process according to the invention is preferably implemented under the following operating conditions: the total pressure is between 0.1 and 10 MPa, and preferably between 0.2 and 7 MPa; the temperature is between 40 and 600° C., and preferably between 100 and 400° C.; the hourly volumetric flow rate (VVH-1) is between 0.01 and 100 h$^{-1}$, and preferably between 0.4 and 20 h$^{-1}$.

It is specified that, according to the invention, the oligomerization process corresponds to an addition that is limited to essentially 2 to 6 monomers or basic molecules, whereby said monomers are olefins.

The following examples illustrate this invention without limiting its scope.

EXAMPLES

In the following examples, the aerosol technique that is used is the one that is described above in the disclosure of the invention.

For each of the examples of the substrates S1 and S3 below, the ratio $V_{inorganic}/V_{organic}$ of the mixture that is obtained from stage b), stage b') or stage b") is calculated. This ratio is defined as follows: $V_{inorganic}/V_{organic}=(m_{inorg}*\rho_{org})/(m_{org}*\rho_{inorg})$ where $m_{inorg}$ is the final mass of the inorganic fraction in condensed oxide form, namely $SiO_2$ and $AlO_2$, in the solid elementary particle that is obtained by atomization; $m_{org}$ is the total mass of the non-volatile organic fraction that is found in the solid elementary particle that is obtained by atomization, namely the surfactant and the structuring agent; $\rho_{org}$ and $\rho_{inorg}$ are the densities that are respectively combined with non-volatile organic and inorganic fractions. In the following examples, it is considered that $\rho_{org}=1$ and $\rho_{inorg}=2$. Also, the ratio $V_{inorganic}/V_{organic}$ is calculated as being equal to $V_{inorganic}/V_{organic}=(m_{SiO2}+m_{AlO2})/[2*(m_{structuring\ agent}+m_{surfactant})]$. Ethanol, soda, and water do not come into play in the calculation of said ratio $V_{inorganic}/V_{organic}$.

Example 1

Preparation according to the first process for preparation of the material that is present in the catalyst according to the invention of a material M1 with hierarchized and organized porosity in the fields of microporosity and mesoporosity whose microporous and crystallized walls consist of ZSM-5-type aluminosilicate zeolitic entities such as the Si/Al molar ratio=49.

6.86 g of a tetrapropylammonium hydroxide solution (TPAOH 40% by mass in an aqueous solution) is added to 037 g of aluminum sec-butoxide (Al(O$^s$C$_4$H$_9$)$_3$). After 30 minutes of vigorous stirring at ambient temperature, 27 g of demineralized water and 18.75 g of tetraethylorthosilicate (TEOS) are added. The whole mixture is left under vigorous stirring at ambient temperature for 18 hours so as to obtain a clear solution. A solution that contains 66.61 g of ethanol, 61.24 g of water, and 5.73 g of surfactant F127 (pH of the mixture=13.5) is then added to this solution. The ratio $V_{inorganic}/V_{organic}$ of the mixture is equal to 0.32. The whole mixture is left under vigorous stirring for 10 minutes. The mass is sent into the atomization chamber of the aerosol generator as it has been described in the description above, and the solution is sprayed in the form of fine droplets under the action of carrier gas (dry air) introduced under pressure (P=1.5 bar). The droplets are dried according to the protocol that is described in the disclosure of the invention above: they are conveyed via an $O_2/N_2$ mixture into PVC pipes. They are then introduced into a furnace that is adjusted to a drying temperature set at 350° C. The collected powder is then dried for 18 hours in the oven at 95° C. 100 mg of this powder is placed in a 1 l autoclave in the presence of 0.6 ml of distilled water. The autoclave is brought to 95° C. for 48 hours. The powder is then dried at 100° C. in the oven and then calcined in air for 5 hours at 550° C. The solid is characterized by low-angle and large-angle XRD, by nitrogen volumetric analysis, by TEM, by SEM, and by XF. The TEM analysis shows that the final material has an organic mesoporosity that is characterized by a vermicular structure. The analysis by nitrogen volumetric analysis combined with the analysis by the method $\alpha_s$ leads to a value of the micropore volume $V_{micro}$ (N$_2$) of 0.19 ml/g, a value of the mesopore volume $V_{meso}$ (N$_2$) of 0.48 ml/g, and a specific surface area of the final material of S=760 m$^2$/g. The mesopore diameter $\phi$ that is characteristic of the mesostructured matrix is 6.5 nm. The small-angle XRD analysis leads to the display of a correlation peak at the angle 2$\theta$=0.79°. Bragg's equation $2d*\sin(\theta)=1.5406$ makes it possible to calculate the distance d for correlation between the organized mesopores of the material, or d=11 nm. The thickness of the walls of the mesostructured material defined by e=d–$\phi$ is therefore e=4.5 nm. The large-angle XRD analysis leads to the display of diffraction peaks with angles 2$\theta$=7.9° and 8.9° that are compatible with the crystalline structure MFI of the ZSM-5 zeolite. The Si/Al molar ratio that is obtained by XF is 49. A SEM picture of the thus obtained spherical elementary particles indicates that these particles have a size that is characterized by a diameter that varies from 50 to 3,000 nm, whereby the size distribution of these particles is centered around 300 nm. The thus synthesized material is used in powder form.

The material M1 is thus obtained.

Example 2

Preparation according to the second process for preparation of the material that is present in the catalyst according to the invention of a material M2 with hierarchized and organized porosity in the fields of microporosity and mesoporosity whose microporous and crystallized walls consist of ZSM-5-type aluminosilicate zeolitic entities such as the Si/Al molar ratio=49.

6.86 g of a solution of tetrapropylammonium hydroxide (TPAOH 40% by mass in an aqueous solution) is added to 0.37 g of aluminum sec-butoxide (Al(O$^s$C$_4$H$_9$)$_3$). After 30 minutes of vigorous stirring at ambient temperature, 27 g of demineralized water and 18.75 g of tetraethylorthosilicate (TEOS) are added. The whole mixture is left under vigorous stirring at ambient temperature for 18 hours. This solution is placed in an oven at 80° C. for 25 hours so as to obtain a colloidal solution that contains ZSM-5-type zeolite nanocrystals that have a size close to 50 nm (analysis by light diffusion and by TEM). A solution that contains 66.61 g of ethanol, 61.24 g of water, and 0.17 g of surfactant F127 (pH of the mixture=13.5) is then added to this suspension that is cooled to ambient temperature. The ratio $V_{inorganic}/V_{organic}$ of the mixture is equal to 0.92. The whole mixture is left under vigorous stirring for 10 minutes. The mass is sent into the atomization chamber of the aerosol generator as it has been described in the description above, and the solution is sprayed in the form of fine droplets under the action of carrier gas (dry air) that is introduced under pressure (P=1.5 bar). The droplets are dried according to the protocol that is described in the disclosure of the invention above: they are conveyed via an $O_2/N_2$ mixture into PVC pipes. They are then introduced into a furnace that is adjusted to a drying temperature set at 350° C. The collected powder is then dried for 18 hours in the oven at 95° C. 100 mg of this powder is placed in a 1 l autoclave in the presence of 0.6 ml of distilled water. The autoclave is brought to 95° C. for 48 hours. The powder is then dried at 100° C. in the oven and then calcined in air for 5 hours at 550° C. The solid is characterized by large-angle XRD, by nitrogen volumetric analysis, by TEM, by SEM, and by XF. The TEM analysis shows that the final material has an organized mesoporosity that is characterized by a vermicular structure. The analysis by nitrogen volumetric analysis combined with the analysis by the method $\alpha_s$ leads to a value of the micropore volume $V_{micro}$ ($N_2$) of 0.15 ml/g, a value of the mesopore volume $V_{meso}$ ($N_2$) of 0.55 ml/g, and a specific surface area of the final material of S=310 m$^2$/g. The mesopore diameter $\phi$ that is characteristic of the mesostructured matrix is 19 nm. The TEM analysis coupled with the nitrogen adsorption volumetric analysis leads to a value of the thickness of the walls on the order of 50 nm. The large-angle XRD analysis leads to the display of diffraction peaks at angles 2θ=7.9° and 8.9° that are compatible with the MFI crystalline structure of the ZSM-5 zeolite. The Si/Al molar ratio that is obtained by XF is 49. A SEM picture of the thus obtained spherical elementary particles indicates that these particles have a size that is characterized by a diameter that varies from 50 to 3,000 nm, whereby the size distribution of these particles is centered around 300 nm. The thus synthesized material is used in powder form.

The material M2 is thus obtained.

Example 3

Preparation according to the third process for preparation of the material that is present in the catalyst according to the invention of a material M3 that is hierarchized and organized in the fields of microporosity and mesoporosity and whose macroporous and crystallized walls consist of beta zeolite zeolitic entities (BEA) such as the Si/Al molar ratio=29.

2.37 g of a solution of tetraethylammonium hydroxide (TEAOH 40% by mass in an aqueous solution) is added to 0.48 g of aluminum sec-butoxide (Al(O$^s$C$_4$H$_9$)$_3$). After 30 minutes of vigorous stirring at ambient temperature, 8.94 g of demineralized water and 5.97 g of tetraethylorthosilicate (TEOS) are added. The whole mixture is left under vigorous stirring at ambient temperature for 5 days so as to obtain a clear solution. 3.6 g of crude synthesis beta zeolite nanocrystals (BEA) (Si/Al=60), with a size equal to 40 nm, is added to this solution and dispersed by sonification for 1 hour. A solution that contains 66.61 g of ethanol, 61.24 g of water, and 0.23 g of surfactant F127 (pH of the mixture=11.5) is then added. The ratio $V_{inorganic}/V_{organic}$ of the mixture is equal to 2.38. The whole mixture is left under stirring for 10 minutes; and the dispersion of the crystals is completed by sonification for 30 minutes. The mass is sent into the atomization chamber of the aerosol generator as it has been described in the description above, and the solution is sprayed in the form of fine droplets under the action of carrier gas (dry air) introduced under pressure (P=1.5 bar). The droplets are dried according to the protocol that is described in the disclosure of the invention above: they are conveyed via an $O_2/N_2$ mixture into PVC pipes. They are then introduced into a furnace that is adjusted to a drying temperature set at 350° C. The collected powder is then dried for 18 hours in the oven at 95° C. 100 mg of this powder is placed in a 1 l autoclave in the presence of 0.6 ml of distilled water. The autoclave is brought to 95° C. for 48 hours. The powder is then dried at 100° C. in the oven and then calcined in air for 5 hours at 550° C. The solid is characterized by large-angle XRD, by nitrogen volumetric analysis, by TEM, by SEM, and by XF. The TEM analysis shows that the final material has an organized mesoporosity that is characterized by a vermicular structure. The analysis by nitrogen volumetric analysis combined with the analysis by the method $\alpha_s$ leads to a value of the micropore volume $V_{micro}$ ($N_2$) of 0.21 ml/g, a value of the mesopore volume $V_{meso}$ ($N_2$) of 0.41 ml/g, and a specific surface area of the final material of S=410 m$^2$/g. The mesopore diameter $\phi$ that is characteristic of the mesostructured matrix is 18 nm. The TEM analysis coupled with the nitrogen adsorption volumetric analysis leads to a value of the thickness of the walls on the order of 50 nm. The large-angle XRD analysis leads to the display of diffraction peaks at the angle 2θ=7.7° that is compatible with the BEA crystalline structure of the beta zeolite. The Si/Al molar ratio that is obtained by XF is 29. A SEM picture of the thus obtained spherical elementary particles indicates that these particles have a size that is characterized by a diameter that varies from 50 to 3,000 nm, whereby the size distribution of these particles is centered around 300 nm. The thus synthesized material is used in powder form.

The material M3 is thus obtained.

Example 4

Preparation of the Catalysts C1, C2, and C3

The catalysts C1, C2 or C3 according to the invention are prepared with the materials M1, M2 or M3 and an aluminum binder. The alumina content of each catalyst is adjusted for working with the same Brønsted acid site (protonic) per unit of volume of catalyst. The catalysts C1, C2 or C3 that are thus prepared contain 90% by weight, 90% by weight or 65% by weight of material M1, M2 or M3, whereby the rest is γ-alumina. The catalysts are shaped by extrusion. The extrudates that are obtained are cylindrical with a diameter of 1.6 mm. They are dried at 120° C. and then calcined in air in a flushed bed at 450° C.

Example 5

Catalytic Evaluation of the Catalysts C1, C2 and C3

The performances of the catalysts C1, C2 and C3, prepared according to Example 4, have been evaluated for the oligomerization reaction of a light olefin fraction that contains 58% by weight of C4 olefins in a mixture of paraffins.

The operating conditions of the tests are as follows:

Total pressure: 6 MPa

VVH (h$^{-1}$) [volume of catalyst/volumetric flow rate of feedstock]: 1 h$^{-1}$ The catalysts are activated in advance in situ in $N_2$ at 450° C. for two hours. For each catalytic test, the temperature is adjusted so as to obtain a conversion of the C4 olefins of 99%. The gasoline or gas oil yields are calculated starting from the mass percentage of the oligomerates formed from the 80-155° C. fraction or the 155-370° C. fraction, both being present in the liquid effluent at the end of the implementation of the oligomerization reaction.

The catalytic performance levels of the catalysts C1, C2 and C3 are reported in

TABLE 1

Performance Levels of the Catalysts C1, C2 and C3.

| | C1 | C2 | C3 |
|---|---|---|---|
| Temperature for a Conversion of 99% of Olefinic C4 (° C.) | 235 | 240 | 220 |
| Gasoline Fraction Yield in the Liquid Fraction (% by Weight) | 57 | 59 | 69 |
| Gas Oil Fraction Yield in the Liquid Fraction (% by Weight) | 43 | 41 | 31 |
| Cetane Index | 48.1 | 47.5 | 32.0 |

The catalytic performance levels that are presented in Table 1 demonstrate that the catalysts C1, C2 and C3 according to the invention make it possible to obtain high gas oil fraction yields. The quality of the gas oil fraction that is obtained, characterized by its cetane index (CI), is, furthermore, satisfactory.

The invention claimed is:

1. A process for oligomerization of an olefinic feedstock that contains hydrocarbon molecules having 2 to 12 carbon atoms per molecule comprising conducting said oligomerization in the presence of a catalyst that comprises at least one binder and at least one crystallized material with hierarchized and organized porosity in the ranges of microporosity and mesoporosity, whereby said crystallized material comprises at least two elementary spherical particles, each of said particles comprising a mesostructured silicon-oxide-based matrix having a uniform diameter of mesopores of between 1.5 and 30 nm and having microporous and crystallized walls with a thickness of between 1 and 50 nm, whereby said elementary spherical particles have a maximum diameter of 200 microns,
wherein said crystallized walls of said matrix consist exclusively of zeolitic entities, and
wherein the at least one crystallized material with hierarchized and organized porosity of the catalyst is obtained by process (I), (II), or (III) wherein process (I), (II), or (III) comprise the following:

Process (I):
preparing a clear solution comprising at east one structuring agent, at least one silicic precursor, and at least one precursor of least one element selected from the group consisting of aluminum, iron, boron, germanium and titanium, wherein said clear solution is aqueous or aquo-organic, wherein the structuring agent is basic or the reaction medium is basified by the addition of alkaline metal hydroxide, and wherein said clear solution is prepared under hydrothermal conditions and under an autogenous pressure at a temperature of from ambient temperature to 200° C.,
mixing at least one surfactant and said clear solution to form a solution wherein the ratio of the volumes of inorganic and organic materials $V_{inorganic}/V_{organic}$ is between 0.26 and 4, and wherein the solution has pH greater than 9,
atomizing said solution by aerosol generation wherein said atomization forms spherical droplets,
drying of said droplets to obtain particles,
autoclaving of said particles,
drying said particles, and
eliminating said structuring agent and said surfactant and obtaining a crystallized material with a hierarchized and organized microporosity and mesoporosity;

Process (II):
preparing a reaction mixture comprising at least one structuring agent, at least one silicic precursor, and at least one precursor of at least one element selected from the group consisting of aluminum, iron, boron, germanium and titanium, wherein said reaction mixture is aqueous or aquo-organic, wherein the structuring agent is basic or the reaction medium is basified by the addition of alkaline metal hydroxide, and wherein said reaction mixture is prepared under hydrothermal conditions and under an autogenous pressure at a temperature of from ambient temperature to 200° C., to obtain a colloidal solution comprising zeolitic nanocrystals with a maximum nanometric size of 60 nm and wherein said nanocrystals are dispersed,
solubilizing at least one surfactant and said colloidal solution into a second solution wherein the ratio of the volumes of inorganic and organic materials $V_{inorganic}/V_{organic}$ is between 0.26 and 4, and wherein the second solution has pH greater than 9,
atomizing said second solution by aerosol generation wherein said atomization forms spherical droplets,
drying said droplets, and
eliminating said structuring agent and said surfactant and obtaining a crystallized material with a hierarchized and organized microporosity and mesoporosity; and Process (III):
dispersing zeolitic crystals in solution to obtain a colloidal solution of zeolitic nanocrystals with a maximum nanometric size of 60 nm,
mixing in solution at least one surfactant, said colloidal solution, and at least one clear solution comprising precursor elements of zeolitic entities wherein said precursor elements of zeolitic entities are at least one structuring agent, at least one silicic precursor, and at least one precursor of at least one element selected from the group consisting of aluminum, iron, boron, germanium, and titanium to obtain a second solution, wherein the ratio of the volumes of inorganic and organic materials $V_{inorganic}/V_{organic}$ in the second solution is between 0.26 and 4 and wherein the solution has pH greater than 9,
atomizing said second solution by aerosol generation wherein said atomization forms spherical droplets,
drying said droplets to obtain particles,
autoclaving said particles in the presence of a solvent wherein the volume of the solvent is from 0.01% to 20% relative to the volume of the selected autoclave at a temperature from 50° C. to 200° C. for 1 to 196 hours,
drying said particles in an oven at a temperature of 50° C. to 150° C.,
eliminating said structuring agent and said surfactant and obtaining a crystallized material with a hierarchized and organized microporosity and mesoporosity, and
mixing said crystallized material with hierarchized and organized porosity with at least one element of group VIB and/or group VIII of the Periodic Table.

2. A process according to claim 1, such that the diameter of the mesopores of said matrix is between 4 and 30 nm.

3. A process according to claim 1, further comprising at least one metal selected from among the group consisting of metals of groups IA, IIA, IIB, and VIIB.

4. A process according to claim 1, wherein the silicon-oxide-based matrix comprises at least one element X wherein X is aluminum, iron, boron, titanium or germanium.

5. A process according to claim 4, wherein the element X is aluminum.

6. A process according to claim 1, wherein said crystallized material with hierarchized porosity has a specific surface area of between 70 and 1,100 m²/g.

7. A process according to claim 1 wherein the binder is selected from the group that is formed by alumina, silica, silica-alumina, clays, magnesia, titanium oxide, boron oxide, zirconia, aluminum phosphates, titanium phosphates, zirconium phosphates and carbon.

8. A process according to claim 1, comprising at least one metal selected from among the metals of groups IA, IIA, IIB, VIIB and VIII.

9. A process according to claim 1, wherein the content by weight of said crystallized material is between 50 and 99%.

10. A process according to claim 1, wherein the catalyst is in the form of extrudates with a diameter of between 0.5 and 5 mm.

11. An oligomerization process according to claim 1, wherein said olefinic feedstock contains 20% to 100% by weight of olefins.

12. An oligomerization process according to claim 1 implemented under the following operating conditions: total pressure is between 0.1 and 10 MPa, temperature is between 40 and 600° C., and hourly volumetric flow rate (VVH) is between 0.01 and 100 h$^{-1}$.

13. A process according to claim 1, wherein said olefinic feedstock contains 25-80% by weight of olefins.

14. A process according to claim 1, wherein the oligomer product consists essentially of 2 to 6 olefin monomers.

15. A process according to claim 1, wherein the crystallized material of the catalyst is obtained by process (I).

16. A process according to claim 1, wherein the crystallized material of the catalyst is obtained by process (II).

17. A process according to claim 1, wherein the crystallized material of the catalyst is obtained by process (III).

18. A process according to claim 1, wherein the at least one element of process (I), (II), or (III) is aluminum.

* * * * *

UNITED STATES PATENT AND TRADEMARK OFFICE
CERTIFICATE OF CORRECTION

PATENT NO. : 8,785,707 B2
APPLICATION NO. : 12/994194
DATED : July 22, 2014
INVENTOR(S) : Amandine Cabiac et al.

It is certified that error appears in the above-identified patent and that said Letters Patent is hereby corrected as shown below:

In the Claims

Claim 1, Column 31, Line 44 reads: "preparing a clear solution comprising at east one structur-"
should read -- preparing a clear solution comprising at least one structur- --.

Claim 1, Column 31, Line 46 reads: "precursor of least one element selected from the group"
should read -- precursor of at least one element selected from the group --.

Signed and Sealed this
Twenty-seventh Day of January, 2015

Michelle K. Lee
*Deputy Director of the United States Patent and Trademark Office*